United States Patent
Bazin-Lee et al.

(10) Patent No.: US 11,274,115 B2
(45) Date of Patent: Mar. 15, 2022

(54) IMIDAZOQUINOLINE DERIVATIVES AND THEIR USE IN THERAPY

(71) Applicant: GLAXOSMITHKLINE BIOLOGICALS SA, Rixensart (BE)

(72) Inventors: Helene G. Bazin-Lee, Hamilton, MT (US); Jay T. Evans, Hamilton, MT (US); David Burkhart, Hamilton, MT (US); Michael Cochran, Hamilton, MT (US); David A. Johnson, Hamilton, MT (US)

(73) Assignee: GLAXOSMITHKLINE BIOLOGICAL SA, Rixensart (BE)

( * ) Notice: Subject to any disclaimer, the term of this patent is extended or adjusted under 35 U.S.C. 154(b) by 435 days.

(21) Appl. No.: 16/330,599

(22) PCT Filed: Sep. 5, 2017

(86) PCT No.: PCT/EP2017/072152
§ 371 (c)(1),
(2) Date: Mar. 5, 2019

(87) PCT Pub. No.: WO2018/046460
PCT Pub. Date: Mar. 15, 2018

(65) Prior Publication Data
US 2021/0277038 A1      Sep. 9, 2021

Related U.S. Application Data

(60) Provisional application No. 62/384,618, filed on Sep. 7, 2016.

(51) Int. Cl.
*C07F 9/6561* (2006.01)

(52) U.S. Cl.
CPC ................ *C07F 9/6561* (2013.01)

(58) Field of Classification Search
CPC .................................. C07F 9/6561
See application file for complete search history.

(56) References Cited

U.S. PATENT DOCUMENTS

| | | | |
|---|---|---|---|
| 7,897,597 B2 * | 3/2011 | Lindstrom | A61P 35/00 514/227.8 |
| 8,624,029 B2 * | 1/2014 | Johnson | C07F 9/6561 546/23 |

FOREIGN PATENT DOCUMENTS

| | | |
|---|---|---|
| WO | 2005020999 A1 | 3/2005 |
| WO | 2007100634 A2 | 9/2007 |
| WO | 2010048520 A1 | 4/2010 |
| WO | 2012031140 A1 | 3/2012 |
| WO | 2017102652 A1 | 6/2017 |
| WO | 2017102654 A1 | 6/2017 |

OTHER PUBLICATIONS

Anwar "Recent clinical trends in Toll-like receptor targeting therapeutics" Medicinal Research Reviews 2019;39: 1053-1090.*
Kaushik "Structural evolution of toll-like receptor 7/8 agonists from imidazoquinolines to imidazoles" RSC Med. Chem., 2021, 12, 1065.*
Hunt Further exploration of the structure-activity relationship of imidazoquinolines; identification of potent C7-substituted imidazoquinolines Bioorg. Med. Chem. Lett., 2020, 30, 126788.*
Gerster "Synthesis and Structure-Activity-Relationships of 1H-Imidazo[4,5-c]quinolines That Induce Interferon Production" J. Med. Chem. 2005, 48, 3481-3491.*

* cited by examiner

*Primary Examiner* — David K O'Dell
(74) *Attorney, Agent, or Firm* — Birch, Stewart, Kolasch & Birch, LLP

(57) ABSTRACT

This invention relates inter alia to novel imidazoquinoline derivatives and their use in therapy, particularly as vaccine adjuvants.

23 Claims, 10 Drawing Sheets

A. Initial Salting Method

1. Dissolve IQ in THF
2. Add salt/MeOH to IQ/THF
3. Evaporation drying
4. High vacuum drying
5. Add 2% glycerol in water
6. Sonicate
7. Sterile filter B. Direct Aqueous Salting Method 1. Dissolve IQ in aqueous vehicle
2. Add salt dissolved in aqueous vehicle
3. Sonicate
4. Sterile filter C. Dry Salting Method 1. Dissolve IQ in THF
2. Add salt directly to IQ/THF
3. Evaporation drying
4. Add 2% glycerol in water
5. Sonicate
6. Sterile filter

IMIDAZOQUINOLINE DERIVATIVES AND THEIR USE IN THERAPY

STATEMENT REGARDING FEDERALLY SPONSORED RESEARCH

This invention was made with Government support under contract #HHSN272200900036C awarded by the National Institutes of Health. The Government has certain rights in the invention.

FIELD OF THE INVENTION

The present invention relates to novel imidazoquinoline derivatives, processes for their preparation, compositions containing them, and their use in therapy especially as vaccine adjuvants.

BACKGROUND OF THE INVENTION

The refinement and simplification of microbial vaccines and the use of synthetic and recombinant subunit antigens to improve vaccine manufacturability and safety has resulted in a decrease in vaccine potency. This has led to studies on the co-administration of adjuvants with antigens to potentiate vaccine activity and the weak immunogenicity of synthetic and recombinant epitopes. Adjuvants are additives that enhance humoral and/or cell-mediated immune responses to a vaccine antigen. The design of vaccine adjuvants, however, has historically been difficult because of the complex nature of the molecular mechanisms involved in immune system function. Although the addition of microbial components has long been known to enhance adaptive immune responses, only recently was it shown that toll-like receptors (TLRs) on cells involved in immune surveillance, such as epithelial and dendritic cells, engage many of these microbial products via so-called "pathogen-associated patterns" or PAMPs. Many vaccine adjuvants and stand-alone immunomodulators appear to interact with members of the TLR family.

Of the 10 known TLRs that have been identified in humans, five are associated with the recognition of bacterial components (TLRs 1, 2, 4, 5, 6) and four others (TLRs 3, 7, 8, 9) appear to be restricted to cytoplasmic compartments and are involved in the detection of viral RNA (TLRs 3, 7, 8) and unmethylated DNA (TLR9) (Iwasaki, A., *Nat Immunol* 2004, 5, 987). Activation of TLRs regulates intracellular signaling pathways and leads to gene expression via interaction with intracellular adapter molecules such as MyD88, TRIF, TIRAP, and TRAM (Akira, S. *Nat Rev Immunol* 2004, 4, 499; Takeda, K. *Semin Immunol* 2004, 16, 3). These adapter molecules can differentially regulate the expression of inflammatory cytokines/chemokines and type I interferons (IF$\alpha$/$\beta$), which can lead to the preferential enhancement of antigen-specific humoral and cell-mediated immune responses (Zughaier, S. *Infect Immun* 2005, 73, 2940). Humoral immunity is the major line of defense against bacterial pathogens, whereas the induction of cytotoxic T lymphocytes (CTLs) appears to be crucial for protective immunity in the case of viral disease and cancer.

In the case of TLR7 and TLR8 activation, a few different classes of small molecule mimetics of the natural (U- and/or G-rich) viral ssRNA ligands have been identified. These include certain antiviral compounds related to oxidized guanosine metabolites (oxoguanosines), which primarily interact with TLR7 (Heil, F. *Eur J Immunol* 2003, 33, 2987; Hemmi, 2002) and derivatives of adenine which engage TLR7 and/or TLR8. The immune stimulating ability of these compounds has been attributed to the TLR/MyD88-dependent signaling pathways and the production of cytokines, including IL-6 and type I (particularly interferon-$\alpha$) and II interferons. TLR7 or TLR8 activation leads to the upregulation of co-stimulatory molecules (e.g. CD-40, CD-80, CD-86) and class I and II MHC molecules on dendritic cells (DCs). DCs are the principal cells of the immune system involved in uptake and presentation of antigens to T lymphocytes. Plasmacytoid dendritic cells (pDCs), which preferentially express TLR7, are professional interferon-$\alpha$ producing cells; whereas mDCs express TLR8 only. TLR8 activation on mDCs leads to the preferential production of pro-inflammatory cytokines such as IL-12, TNF-$\alpha$, and IFN-$\gamma$ and cell-mediated immunity (CMI). It has been shown that TLR7 agonists are more effective at generating IFN-$\alpha$ and IFN-regulated cytokines, whereas TLR8 agonists, which lead to the reversal of CD4+ regulatory (Treg) cell function, are more effective at inducing proinflammatory cytokines such as TNF-$\alpha$ and IL-12, suggesting that TLR7 activation may be more important for antibody responses (Th2-type responses) while TLR8 activation should induce CMI or Th1-type immune responses (Gordon *J Immunol* 2005, 1259).

One class of TLR-active adenine derivatives that has received a considerable amount of attention are the 1H-imidazo[4,5-c]quinolines. The prototypical member of this class, imiquimod, was found to be effective against genital papilloma virus infections, actinitic keratosis and basal cell carcinoma when applied topically in cream form. Imiquimod, however, has relatively low interferon inducing activity in both oral and topical preparations and both oral and topical preparations are not without side effects. In fact, serious side effects were reported in an HCV clinical trial with imiquimod. The large immunological "footprint" of TLR7 agonists in general has led to concerns over toxicity: clinical trials with another TLR7 agonist ANA-975, an oxoguanosine derivative, were suspended due to toxicity issues.

Another member of the 1H-imidazo[4,5-c]quinolone class of TLR7/8 ligands is resiquimod. Resiquimod also activates TLR7 in macrophages and DCs in a MyD88-dependent manner either directly or indirectly via an accessory molecule and upregulates co-stimulatory molecules and MHCI/II in DCs. In contrast to imiquimod, the more potent and toxic resiquimod is also a ligand for TLR8 signaling, which leads to the reversal of CD4+ regulatory (Treg) cell function.

Lipid conjugates of nucleoside drugs are known in the art to enhance oral bioavailability in general as well as to permit incorporation of the resulting "nucleolipid" into lipid membranes of liposomes (Rosemeyer, H. *Chemistry & Biodiversity* 2005, 2, 977-1063). Incorporating sensitive and/or highly active molecules in liposomes establishes a slow release carrier system or molecular depot which protects the molecule from degradation and decreases toxic side effects. It has often been found, however, that lipid conjugates are less biologically active than the parent molecule.

Certain lipidated imidazoquinoline derivatives have been described in U.S. Pat. No. 8,624,029 (Johnson) and these compounds have advantages over corresponding unlipidated analogues.

It remains an objective to discover further effective and safe vaccine adjuvants.

BRIEF DESCRIPTION OF THE INVENTION

Herein we describe novel lipidated imidazoquinoline derivatives. The compounds of the invention have been shown to be inducers of cytokines such IFN-α, IFN-γ and TNF-α and to be agonists of TLR7 and/or TLR8. These compounds are expected to be useful as vaccine adjuvants in the therapeutic or prophylactic treatment of inter alia infectious diseases and cancer.

BRIEF DESCRIPTION OF THE FIGURES

FIG. 18 shows a schematic representation of salting methods, as described herein.

DETAILED DESCRIPTION OF THE INVENTION

Figure 1:
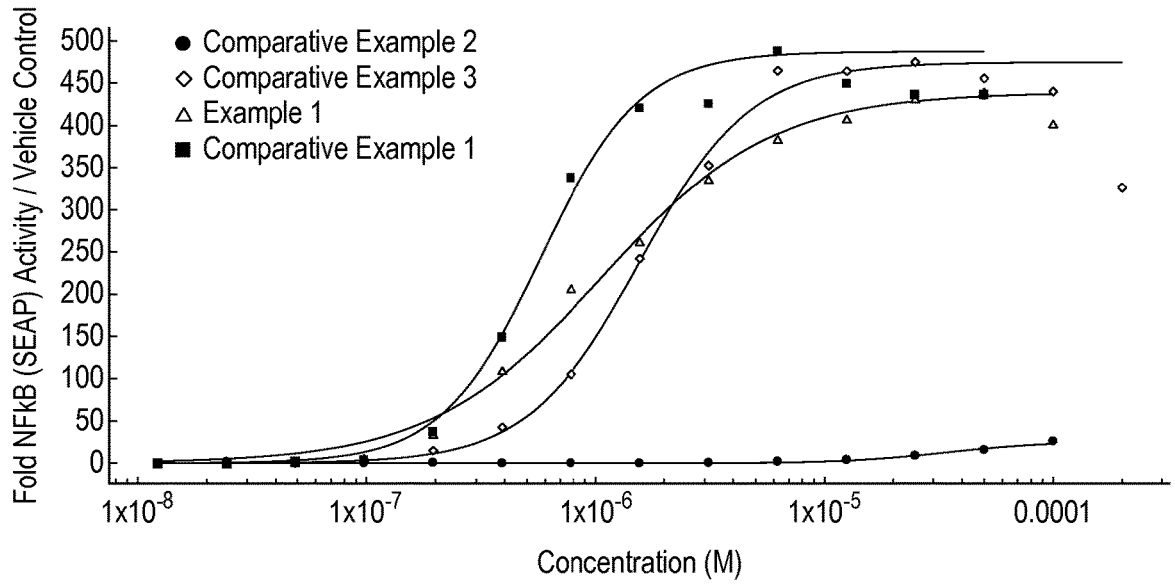
FIG. 1 shows a plot of curves of various compounds tested in the hTLR7 agonist reporter assay in HEK293 cells.

Throughout this application, references are made to various embodiments relating to compounds, compositions, and methods. The various embodiments described are meant to provide a variety of illustrative examples and should not be construed as descriptions of alternative species. Rather it should be noted that the descriptions of various embodiments provided herein may be of overlapping scope. The embodiments discussed herein are merely illustrative and are not meant to limit the scope of the present invention.

It is to be understood that the terminology used herein is for the purpose of describing particular embodiments only and is not intended to limit the scope of the present invention. In this specification and in the claims that follow, reference will be made to a number of terms that shall be defined to have the following meanings.

"Alkyl" refers to monovalent saturated aliphatic hydrocarbyl groups having, according to various embodiments, up to 24 carbon atoms and, in some embodiments, from 1 to 6 carbon atoms and, in further embodiments, from 2 to 6 carbon atoms. "($C_x$-$C_y$)alkyl" refers to alkyl groups having from x to y carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

"Alkylene" means a divalent saturated aliphatic hydrocarbyl groups having, according to various embodiments, from 2 to 6 carbon atoms. This term includes, by way of example, linear and branched hydrocarbyl groups such as ethylene (—$CH_2CH_2$—), n-propylene (—$CH_2CH_2CH_2$—), isopropylene (—$CH(CH_3)CH$—), n-butylene (—$CH_2CH_2CH_2CH_2$—), isobutylene (—$CH(CH_3)CHCH_2$—), sec-butylene ($CH(CH_3CH_2)CH$—) and n-pentylene (—$CH_2CH_2CH_2CH_2CH_2$—).

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Amino" refers to the group —$NHR^6$ where $R^6$ is independently selected from hydrogen, $C_{1-6}$ alkyl and $C_{2-6}$ alkenyl, and typically represents H or Me. However, the expression $C_1$-$C_6$ alkylamino means ($C_1$-$C_6$ alkyl)HN—, the expression $C_3$-$C_6$ cycloalkyl$C_1$-$C_6$ alkylamino means ($C_3$-$C_6$ cycloalkyl)($C_1$-$C_6$ alkyl)N- and the expression $C_1$-$C_6$alkoxy$C_1$-$C_6$alkylamino means ($C_1$-$C_6$ alkoxy)($C_1$-$C_6$ alkyl)N—.

"Cycloalkyl" refers to a saturated carbocyclic group of from 3 to 14 carbon atoms (e.g. from 3 to 8 carbon atoms, particularly 3 to 6 carbon atoms) and no ring heteroatoms.

"Cycloalkenyl" refers to an unsaturated carbocyclic group of from 5 to 14 carbon atoms (e.g. from 6 to 8 carbon atoms, such as 6 or 7 carbon atoms) and no ring heteroatoms and containing at least one ring carbon carbon double bond.

"Alkenyl" refers to an unsaturated alkyl group which contains at least one carbon-carbon double bond. For example it may contain one, two or three double bonds but more typically will contain 2 or most usually one double bond.

Unless indicated otherwise, the nomenclature of substituents that are not explicitly defined herein are arrived at by naming the terminal portion of the functionality followed by the adjacent functionality toward the point of attachment. For example, the substituent "$C_3$-$C_6$ cycloalkyl$C_1$-$C_6$ alkoxy" refers to the group ($C_3$-$C_6$ cycloalkyl)-($C_1$-$C_6$ alkoxy)-. It is understood that the above definitions are not intended to include impermissible substitution patterns (e.g., methyl substituted with 5 fluoro groups). Such impermissible substitution patterns are well known to the skilled artisan.

The compounds of the subject invention are described generally by formula (I):

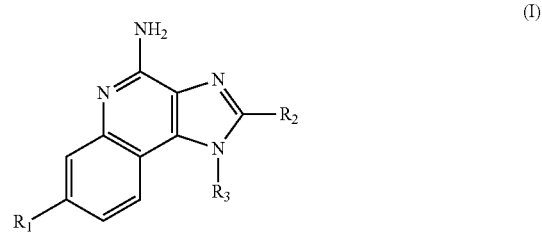

wherein:

$R_1$ represents —O—Z—(P(=O)—OH)—O—Y-A $R_2$ represents H, $C_1$-$C_6$alkyl, $C_1$-$C_6$alkylamino, $C_1$-$C_6$alkoxy, $C_3$-$C_6$cycloalkyl$C_1$-$C_6$ alkyl, $C_3$-$C_6$ cycloalkyl$C_1$-$C_6$ alkylamino, $C_3$-$C_6$ cycloalkyl$C_1$-$C_6$ alkoxy, $C_1$-$C_6$ alkoxy$C_1$-$C_6$ alkyl, $C_1$-$C_6$ alkoxy$C_1$-$C_6$ alkylamino, $C_1$-$C_6$ alkoxy$C_1$-$C_6$ alkoxy; and optionally terminally substituted with a hydroxyl, amino, —NHNH$_2$, N$_3$, —C≡CH, —COOH, or maleimido group;

Z represents (C$_2$-C$_6$ alkyleneO)$_q$;

Y represents (C$_2$-C$_6$ alkyleneO)$_r$;

q represents an integer 1 to 6;

r represents 0 or an integer 1 to 20;

$R_3$ represents C$_2$-C$_6$ alkylene-OH, C$_2$-C$_6$ alkylene-NH$_2$, C$_2$-C$_5$ alkenyl-CH$_2$—OH or C$_2$-C$_5$ alkenyl-CH$_2$—NH$_2$;

A represents

[Structure showing two options: one with —OR$_4$ and —OR$_5$ branches, and another being a cholesterol-like steroid structure with -(C$_2$-C$_6$alkyleneO)$_p$ attachment]

wherein:

$R_4$ represents H, C$_4$-C$_{24}$ alkyl, C$_4$-C$_{24}$ alkenyl, —CO—C$_3$-C$_{23}$ alkyl, or —CO—C$_3$-C$_{23}$ alkenyl;

$R_5$ represents, C$_4$-C$_{24}$ alkyl, C$_4$-C$_{24}$ alkenyl, —CO—C$_3$-C$_{23}$ alkyl, or —CO—C$_3$-C$_{23}$ alkenyl;

p represents 0 or an integer 1 to 6;

or a pharmaceutically acceptable salt thereof.

Suitably $R_2$ represents H, $C_1$-$C_6$ alkyl or $C_1$-$C_6$ alkoxy$C_1$-$C_6$ alkyl, especially H, $C_1$-$C_6$ alkyl or $C_1$-$C_3$ alkoxy$C_1$-$C_3$ alkyl. For example, $R_2$ represents H, n-butyl or —CH$_2$OCH$_2$CH$_3$ especially n-butyl.

Suitably q represents an integer 1 to 3, particularly 1 or 3 and especially 1.

Suitably r represents 0 or an integer 1 to 6 e.g. 0 or an integer 1 to 3, such as 0 or 3 especially 0.

Suitably $R_3$ represents C$_2$-C$_6$ alkylene-OH or C$_2$-C$_6$ alkylene-NH$_2$, particularly C$_2$-C$_6$ alkylene-OH and especially CH$_2$CH$_2$OH.

Suitably p represents an integer 1 to 3.

Suitably A represents

[Structure with —OR$_4$ and —OR$_5$ branches]

In one preferred embodiment, the compounds of the subject invention are described generally by formula (IA):

(IA)

[Imidazoquinoline structure with NH$_2$, $R_2$, $R_3$, and $R_1$ substituents]

wherein:

$R_1$ represents —O—Z—(P(=O)—OH)—O—Y-A $R_2$ represents H, $C_1$-$C_6$ alkyl or $C_1$-$C_3$ alkoxy$C_1$-$C_3$ alkyl;

Z represents (C$_2$-C$_6$ alkyleneO)$_q$;

Y represents (C$_2$-C$_6$ alkyleneO)$_r$;

q represents an integer 1 to 6;

r represents 0 or an integer 1 to 20;

$R_3$ represents C$_2$-C$_6$ alkylene-OH;

A represents

[Structure with —OR$_4$ and —OR$_5$ branches]

wherein:

$R_4$ represents H, —CO—C$_3$-C$_{23}$ alkyl, or —CO—C$_3$-C$_{23}$ alkenyl;

$R_5$ represents, —CO—C$_3$-C$_{23}$ alkyl, or —CO—C$_3$-C$_{23}$ alkenyl;

or a pharmaceutically acceptable salt thereof.

Suitably $R_2$ represents H, n-butyl or CH$_3$CH$_2$OCH$_2$— especially n-butyl.

Suitably Z represents ((CH$_2$)$_2$O)$_q$ especially CH$_2$CH$_2$O or Z represents CH$_2$CH$_2$CH$_2$CH$_2$O, especially CH$_2$CH$_2$O.

Suitably Y represents ((CH$_2$)$_2$O)$_r$.

Suitably q represents an integer 1 to 3, particularly 1 or 3 and especially 1.

Suitably r represents 0 or an integer 1 to 6 e.g. 0 or an integer 1 to 3, such as 0 or 3 especially 0.

Suitably $R_3$ represents —CH$_2$CH$_2$OH.

In one embodiment $R_4$ represents H and $R_5$ represents —CO—C$_3$-C$_{23}$ alkyl, or —CO—C$_3$-C$_{23}$ alkenyl. In an alternative embodiment, $R_4$ and $R_5$ independently represent —CO—C$_3$-C$_{23}$ alkyl or —CO—C$_3$-C$_{23}$ alkenyl.

Suitably $R_4$ and $R_5$ independently represent lauroyl, myristoyl, palmitoyl, oleoyl or linoleoyl, preferably oleoyl or palmitoyl, especially oleoyl. Suitably $R_4$ and $R_5$ are the same.

The compounds of the subject invention may be prepared by reaction of a compound of formula (II):

(II)

[Imidazoquinoline structure with NH$_2$, $R_2$, $R_3$, and $R_{1a}$ substituents]

wherein:
$R_{1a}$ represents —O—Z—H;
and Z, $R_2$ and $R_3$ are defined as for compounds of Formula (I);
or a protected derivative thereof;
with a compound of formula (III)

$P_g$—OP(N-iPr$_2$)—O—Y-A     (III)

wherein A is defined as for compounds of Formula (I) and $P_g$ is a protecting group, typically CNCH$_2$CH$_2$—, followed by oxidation of P(III) to P(V) and removal of protecting groups.

Conditions suitable for performing this reaction include combining the ingredients in the presence of imidazolium triflate (Imid-OTf) in an inert organic solvent such as CH$_2$Cl$_2$. The reaction product can be purified or directly oxidized followed by removal of protecting groups.

Suitably the hydroxyl group of $R_3$ is protected by an acyl group, such as a levulinoyl group. Deprotection may be achieved by treatment with hydrazine.

When $R_4$ represents hydrogen, it may be protected as an ether e.g. with tetrahydropyran (THP). This group may be removed at the desired stage by treatment with acid (e.g. HCl).

Compounds of formula (II) or a protected derivative thereof may be prepared by reaction of a compound of formula (IV)

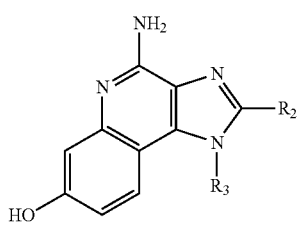

(IV)

wherein:
$R_2$ and $R_3$ are defined as for compounds of formula (I);
or a protected derivative thereof;
with a compound of formula (V)

L$_1$-ZH     (V)

wherein Z is as defined as for compounds of formula (I) and L$_1$ is a leaving group or a protected derivative thereof.

Example leaving groups L$_1$ include halogen such as Br, mesylate, tosylate and the like, especially Br.

Typically the compound of formula (V) will be employed in a form in which the terminal hydroxyl of group Z is protected. Suitable hydroxyl protecting groups include acyl groups such as acetyl or as silyl ethers such as the t-butyldimethylsilyl (TBS) ether, or as ether such as benzyl (Bn) ether.

Conditions for the reaction of compounds of formulae (IV) and (V) include combining the reagents in the presence of cesium carbonate in an organic solvent such as DMF followed by aqueous work-up and purification.

Alternatively, compounds of formula (II) or protected derivatives thereof may be prepared by heating a compound of formula (VI)

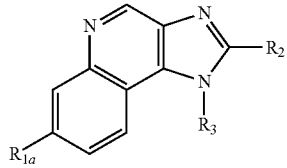

(VI)

wherein:
$R_{1a}$ represents —O—Z—H;
and Z, $R_2$ and $R_3$ are defined as for compounds of formula (I) or a protected derivative thereof with an oxidising agent such as CH$_2$CO$_3$H or 3-chloro-peroxybenzoic acid in an inert solvent such as ethanol or methylene chloride to form an N-oxide followed by reaction to form an activated ester e.g. with pTsCl or methanesulfonyl chloride in an inert solvent such as methylene chloride followed by amination with ammonia or an ammonia derivative such as NH$_4$OH in an inert solvent such as methylene chloride. The reaction also proceeds if the N-oxide is treated with the ammonia or ammonia derivative prior to the pTsCl or methanesulfonyl chloride (or other reagent to form an activated ester).

Suitably the hydroxyl group of $R_3$ is protected by an acyl group, such as a levulinoyl group. Deprotection may be achieved by treatment with hydrazine.

Further details of this conversion may be gleaned by reference to WO05/020999 (the contents of which are herein incorporated by reference in their entirety) and particularly Reaction Scheme 1 where similar processes are described.

Compounds of formula (VI) or a protected derivative thereof may be prepared by reaction of a compound of formula (VII)

(VII)

wherein:
and $R_2$ and $R_3$ are defined as for compounds of formula (I);
or a protected derivative thereof;
with a compound of formula (V)

L$_1$-ZH     (V)

wherein Z is as defined as for compounds of Formula (I) and L$_1$ is a leaving group or a protected derivative thereof.

Typically the compound of formula (V) will be employed in a form in which the terminal hydroxyl of group Z is protected. Suitable hydroxyl protecting groups include esters formed from acyl groups such as acetyl or as silyl ethers such as the t-butyldimethylsilyl (TBS) ether or as ether such as benzyl (Bn) ether.

A suitable leaving group L$_1$ is halogen such as Br, mesylate, tosylate and the like, especially Br.

Exemplary conditions for this reaction are the same as those for the reaction of compounds of formula (IV) and (V).

Suitably the hydroxyl group of $R_3$ is protected by an acyl group, such as a levulinoyl group. Deprotection may be achieved by treatment with hydrazine.

Suitably the phenolic hydroxyl group is protected as an ether group e.g. as the benzyl ether. Deprotection may be achieved by reduction e.g. with H₂ gas over Pd/C.

The synthesis of compounds of formula (IV) and (VII) and protected derivatives thereof is illustrated in Scheme 1 below:

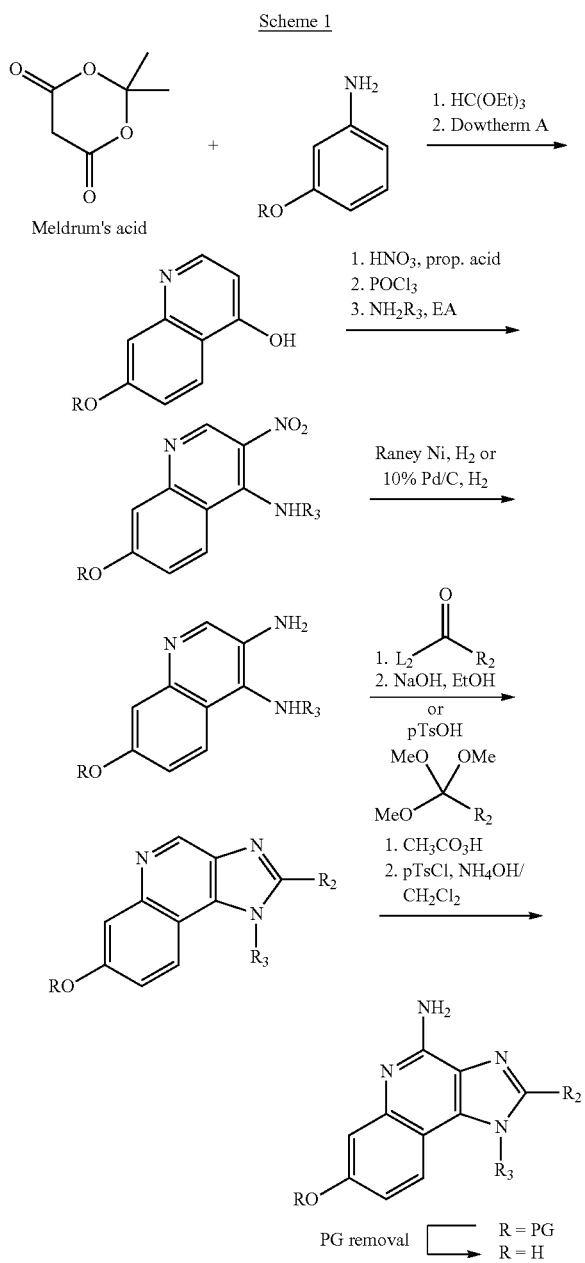

Suitably L₂ is halogen, especially Cl.

Further details of conversions shown in Scheme 1 may be gleaned by reference to WO05/020999 (the contents of which are herein incorporated by reference in their entirety) and particularly Reaction Scheme 1 where similar processes are described.

Compounds of formula (III) or a protected derivative thereof may be prepared by reacting a compound of formula (VIII)

with a compound of formula (IX)

P$_g$OP(N-iPr$_2$)$_2$ (IX)

and P$_g$ is a protecting group, typically CNCH$_2$CH$_2$—.

Conditions for the reaction of compounds of formula (VIII) and (IX) include combining the reagents in an inert solvent such as CH$_2$Cl$_2$ in the presence of tetrazole or other coupling reagent known in the art.

Intermediate compounds of formula (II) and (VI) are new and are claimed as an aspect of the invention. As noted in the examples, compounds of formula (II) and (IV) may have at least some of the biological activity of compounds of formula (I).

Thus the invention provides compound of formula (II):

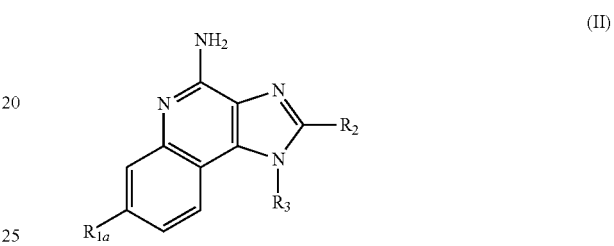

wherein:
R$_{1a}$ represents —O—Z—H;
and Z, R$_2$ and R$_3$ are defined as per compounds of formula (I) and (IA);
or a protected derivative thereof.

The invention also provides a compound of formula (VI)

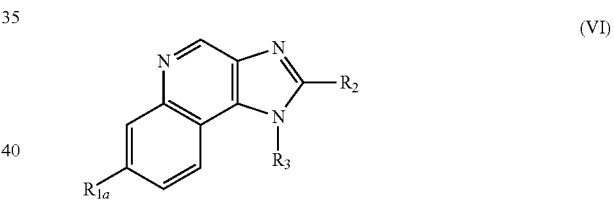

wherein:
R$_{1a}$ represents —O—Z—H;
and Z, R$_2$ and R$_3$ are defined as per compounds of formula (I) and (IA);
or a protected derivative thereof.

In compounds of formula (II), (IV), (VI) and (VII) alcohol groups may be protected as an ester e.g. by reaction with an acyl group (e.g. acetyl or levulinoyl) or may be protected as an ether e.g. as an ether formed with THP or benzyl.

In compounds of formula (II), (IV), (VI) and (VII) amine groups may be protected as an amide e.g. by reaction with an acyl group (e.g. acetyl or levulinoyl).

Compounds of formula (V), (VIII) and (IX) are known or may be prepared by known methods.

The starting compounds and other reagents shown in Scheme 1 are known or may be prepared by known methods.

Pharmaceutically acceptable salts of the compounds of the invention may include acid salts formed with group 1 metal cations (such as sodium and potassium ions) and group 2 metal cations (such as calcium and magnesium ions) as well as with inorganic cations such as ammonium ion or other quaternary ammonium ions (such as choline) and basic salts formed with inorganic anions such as halide (e.g. chloride bromide), phosphate and sulfate and organic anions (e.g. mesylate, succinate, maleate and acetate). Preferred salts are salts formed with choline. In specific embodiments, the salt is a choline bicarbonate salt or a choline hydroxide salt.

The invention also provides methods for making pharmaceutically acceptable salts of a lipidated imidazoquinoline derivative compound. In one embodiment, such salting methods include a method of preparing a choline salt of a lipidated imidazoquinoline derivative, comprising:
    (a) dissolving the compound in an aqueous vehicle;
    (b) adding the choline salt; and
    (c) mixing the compound and choline salt,
wherein, the method does not include the use of an organic solvent. In some embodiments, the method does not include a drying step.

In another embodiment, salting methods of the invention include a method of preparing a choline salt of a lipidated imidazoquinoline derivative, comprising:
    (a) dissolving the compound in an organic solvent;
    (b) adding the choline salt;
    (c) mixing the compound and choline salt,
    (d) removing the organic solvent to produce a dried salt, and
    (e) dissolving the dried salt in an aqueous vehicle;
wherein the method does not include a vacuum drying step. In one embodiment, the organic solvent used in the salting method is tetrahydrofuran (THF). In an additional embodiment, the choline salt is selected from choline bicarbonate and choline hydroxide.

In some embodiments, the lipidated imidazoquinoline derivative is a lipidated imidazoquinoline derivative described herein. In some embodiments, the aqueous vehicle used in the salting methods of the invention is water, optionally containing glycerol (e.g., 1%, 2%, 5% glycerol). In certain embodiments, the choline salt is selected from choline bicarbonate and choline hydroxide.

In some embodiments, the salting methods involve mixing by sonication or mechanical disruption. Mixing is performed for 10 to 120 minutes; preferably 15-90 minutes; more preferably for at least 30 minutes. Mixing is carried out at a temperature between about 20° C. and about 80° C.; such as between about 20, 30 or 40° C. and about 60, 70, or 80° C.

Salting methods of the invention optionally include a sterile filtration step. Sterile filtration can be accomplished, for example, using a 0.22 μm filter, such as a 0.22 μm syringe filter.

Compounds of the subject invention are useful as pharmaceutical substances and particularly as vaccine adjuvants (i.e. as immunostimulants). The invention provides a pharmaceutical composition or a vaccine composition or an immunogenic composition comprising a compound of the invention. Such compositions typically comprise a suitable diluent or carrier, such as water. The composition may be prepared in dry form for making up with water prior to administration. Such compositions may be based on a liposome or other nanoparticle composition in which the compound of the invention is dispersed or an oil in water composition in which the compound of the invention is dispersed. Such compositions may contain other immunostimulants including saponins such as QS21, lipopolysaccharides including MPL and 3D-MPL, CpG oligonucleotides, other TLR7 and TLR8 agonists (such as imiquimod or resiquimod) and combinations thereof.

Such compositions typically contain a vaccine antigen (or more than one). Exemplary antigens include disease antigens including antigens derived from pathogens including viruses (such as HIV, HAV, HBV, HCV, HPV, influenza, human rhinovirus, human syncytial virus), bacteria (such as *Corynebacterium diphtheria, Bordetella pertussis, Clostridium tetani* and toxins secreted thereby, *Mycobacterium tuberculosis, Neisseria* spp., *Meningococcus* spp., *Chlamydia* spp.), and protozoa (such as *Plasmodium* spp.) which cause infectious diseases and cancer antigens (such as MAGE).

In a specific embodiment, the antigen is an influenza antigen e.g. a split influenza antigen such as a pandemic influenza antigen.

In a specific embodiment the antigen is a polysaccharide antigen or a polysaccharide containing antigen.

In further embodiments the compounds of the invention may be administered orally in the form of capsules. In other embodiments the compounds of the invention may be administered topically to a skin or mucosal surface. In such embodiments the compounds of the invention may be combined with conventional topically acceptable diluents.

The invention provides a method of inducing an immune response in a mammal which comprises administering to a mammal in need thereof an immunostimulatory amount of a compound of the invention or a composition containing it (for example a composition described above). The invention also provides a compound of the invention or a composition containing it (for example a composition described above) for use in inducing an immune response in a mammal. The invention also provides use of a compound of the invention or a composition containing it (for example a composition described above) in the manufacture of a medicament for inducing an immune response in a mammal.

The induced immune response may include induction of a type 1 interferon response and/or inducing pro-inflammatory cytokines such as IFN-α and IFN-γ as well as IL-12 and TNF-α.

The invention also provides a method of inducing protective immunity against a disease in a mammal which comprises administering to a mammal in need thereof an immunostimulatory amount of a compound of the invention together with a disease antigen. Disease antigens include antigens derived from pathogens including viruses, bacteria and protozoa which cause infectious diseases mentioned above. The invention also provides a composition comprising a compound of the invention and a disease antigen for use in inducing protective immunity against a disease in a mammal. The invention also provides use of a composition comprising a compound of the invention and a disease antigen in the manufacture of a medicament for inducing protective immunity against a disease in a mammal.

The invention also provides a method of treatment or prophylaxis of cancer in a mammal which comprises administering to a mammal in need thereof an immunostimulatory amount of a compound of the invention together with a cancer antigen. Cancer antigens include antigens associated with or derived from cancers mentioned above. The invention also provides a composition comprising a compound of the invention and a cancer antigen for use in the treatment or prophylaxis of cancer in a mammal. The invention also provides use of a composition comprising a compound of the invention and a cancer antigen in the manufacture of a medicament for the treatment or prophylaxis of cancer in a mammal.

An immunostimulatory amount of a compound of the invention may be between 1 μg and 2 mg, although this amount is illustrative and non-limiting. Thus a vaccine composition may, for example, comprise antigen and 1 μg to 2 mg of a compound of the invention.

The compounds of the invention are expected to have one or more of the following favourable attributes: good agonist activity at hTLR7 and/or hTLR8 (preferably hTLR7 and hTLR8); favourable ratio of TLR7/8 agonist activity; good activity at inducing cytokines e.g. IFN-α, IFN-γ and/or TNF-α, low toxicity; and good chemical and physical stability.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

Abbreviations p-TsOH p-toluenesulfonic acid
p-TsCl p-toluenesulfonyl chloride
THP tetrahydropyran
TBS t-butyldimethylsilyl
HIV human immunodeficiency virus
HAV hepatitis A virus
HBV hepatitis B virus
HCV hepatitis C virus
HPV human papilloma virus
IFN interferon
tet 1H-tetrazole
Lev levulinoyl
TEA triethylamine
CE cyanoethyl
Imid imidazolium
OTf triflate
nBu n-butyl
i-Pr isopropyl
Bn benzyl
t-Bu t-butyl
MeCN acetonitrile
Eq equivalent
M molar
h hour
rt room temperature

EXAMPLES

General Procedure for the Synthesis of Compounds of Formula (I)

Compounds of formula (I) were prepared following the general procedure shown in Scheme 2

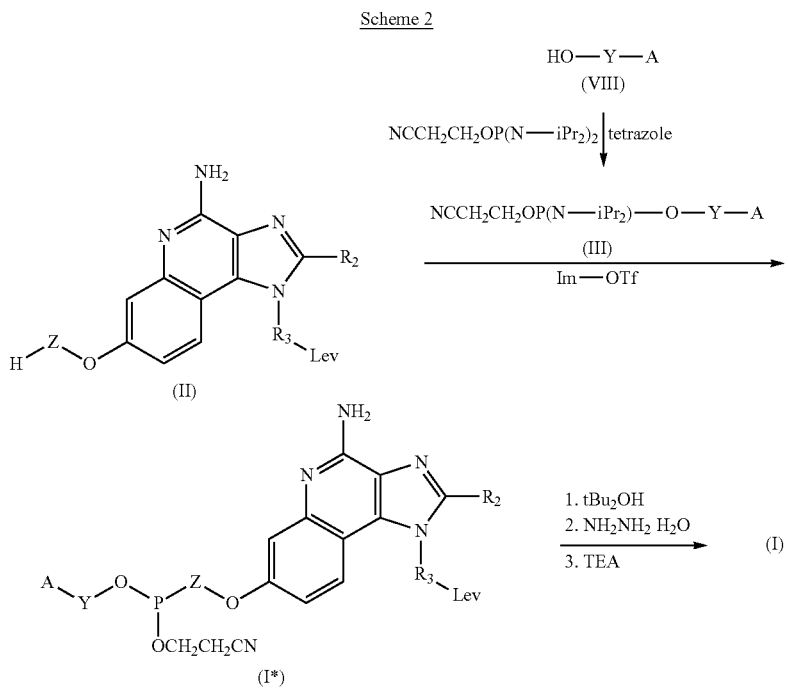

A compound of formula (VIII) (2.0 eq) and 2-cyanoethyl N,N,N',N'-tetraisopropylphosphordiamidite (2.1 eq) were dissolved in anhydrous methylene chloride (0.4 M) at rt. 1H-tetrazole (2.1 eq) was added in four portions over 20 min and the reaction mixture stirred at rt for 1 h. The reaction mixture was cooled to 0° C., imidazoquinoline of formula (II) (1.0 eq) and imidazolium triflate (1.5 eq) were added, and the reaction mixture allowed to warm up to rt. The reaction was usually completed after 1 h at rt and the reaction mixture was purified by chromatography on silica gel (after reducing the volume by concentration under vacuum). The resulting phosphite (I*) was dissolved in chloroform (0.07 M) and oxidized by addition of t-butyl hydroperoxide (1.5 eq). After stirring at rt for 30 min, the reaction mixture was concentrated under vacuum. The levulinoyl group was subsequently deprotected by reacting (I*) in a 4:1 mixture of pyridine:acetic acid (0.05 M) with hydrazine hydrate (5.0 eq). After 5-10 min ar rt, the reaction mixture was cooled to 0° C. and stirred with 2,4-pentanedione (10.0 eq) at 0° C. for 5 min. After aqueous work-up, the dried crude was dissolved in acetonitrile (0.06 M). Triethylamine (acetonitrile:TEA 1:0.35 v:v) was added and the reaction mixture stirred at rt for 6 to 18 h. Once the deprotection was complete, the reaction mixture was filtered over a Büchner filter and the isolated solid rinsed with acetonitrile and dried under high vacuum, or purified by chromatography on silica gel to give compound of formula I.

Example 1
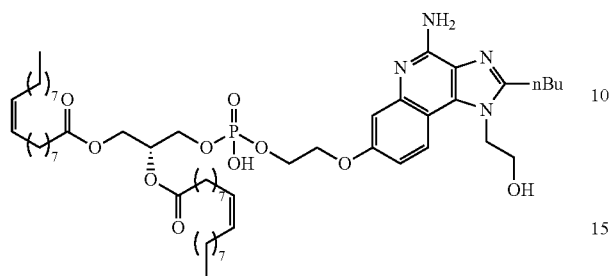
This compound was prepared by following the method of Scheme 3.
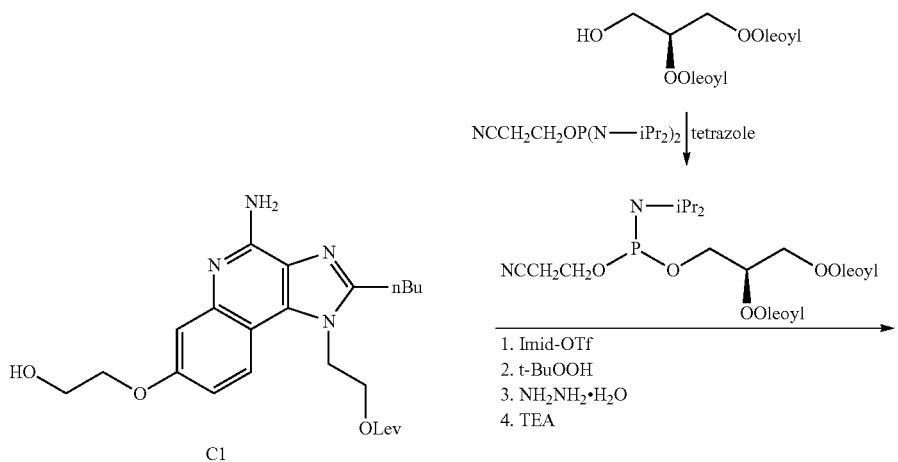
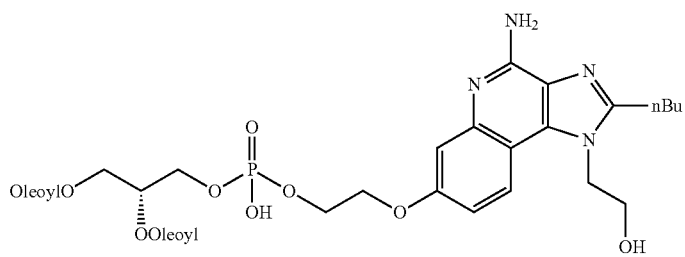
Example 1

C1 was coupled with 1,2-dioleoyl-sn-glycerol following the procedure described in General Procedure 1. After purification by chromatography on silica gel (0 to 10% methanol in chloroform), the corresponding phosphite (I*) was isolated in 66% yield. (I*) was subsequently oxidized with t-butyl peroxide and deprotected sequentially with hydrazine hydrate and TEA as described in General procedure 1 to give Example 1 in 84% yield. $^1$H NMR (400 MHz, CDCl$_3$/CD$_3$OD) δ 7.84 (d, 1H), 7.24 (m, 2H), 5.33 (m, 4H), 5.27 (m, 1H), 4.8 (m, 2H), 4.43 (dd, 1H), 4.39 (m, 2H), 4.22 (dd, 1H), 4.10 (t, 2H), 3.99 (t, 2H), 2.92 (t, 2H), 2.32 (m, 4H), 2.00 (m, 8H), 1.84 (m, 2H), 1.60 (m, 4H), 1.51 (m, 2H), 1.30 (m, 40H) 1.02 (t, 3H), 0.88 (m, 6H); negative ES TOF-MS calc for [M−H]$^-$ 1025.67, found 1025.72.

Example 2

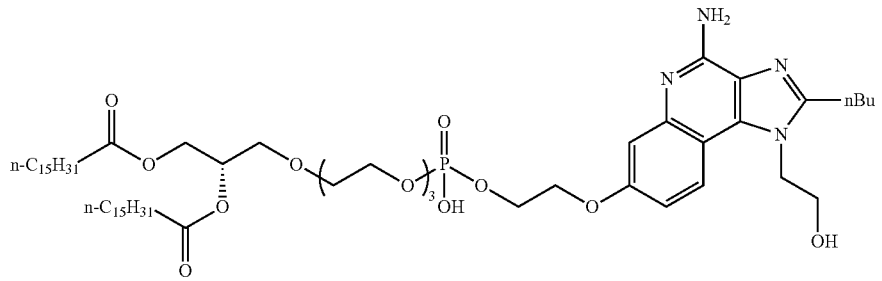

This compound was prepared by following the method of Scheme 4.

Scheme 4

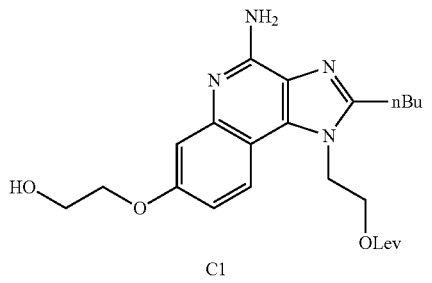

C1

+

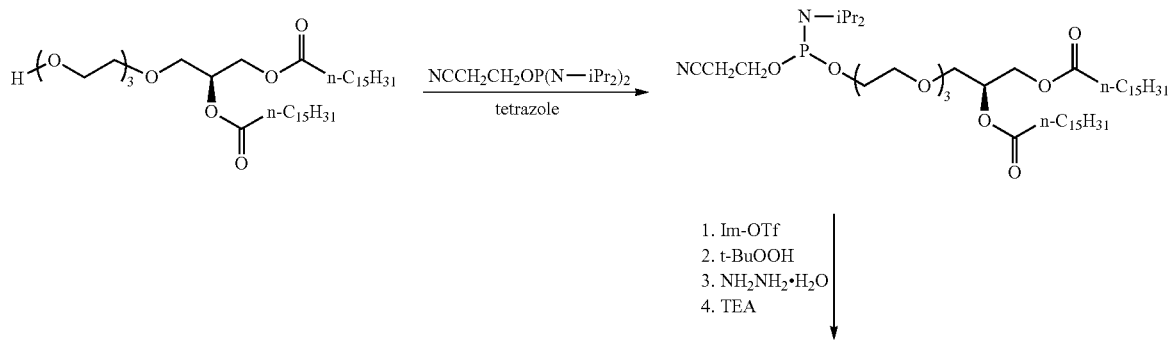

1. Im-OTf
2. t-BuOOH
3. NH$_2$NH$_2$·H$_2$O
4. TEA

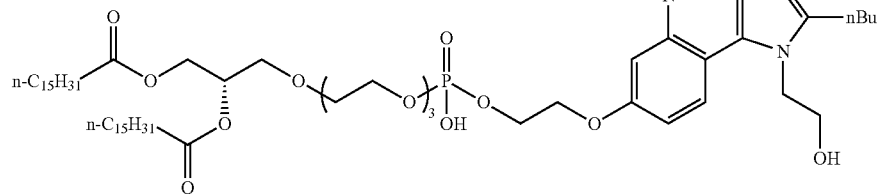

Example 2

C1 was coupled with 1,2-dipalmitoyl-3-triethyleneglycol-sn-glycerol following the procedure described in General Procedure 1. After purification by chromatography on silica gel (0 to 10% methanol in chloroform), the corresponding phosphite (I*) was not isolated clean. Crude (I*) was subsequently oxidized with t-butyl peroxide and the resulting oxidized (I*), obtained in 51% yield after purification by chromatography on silica gel (0 to 15% methanol in chloroform), was deprotected sequentially with hydrazine hydrate and TEA as described in General procedure 1 to give Example 2 in 61% yield after chromatography on silica gel (0 to 40% methanol in chloroform). $^1$H NMR (400 MHz, CDCl$_3$/CD$_3$OD) δ 7.79 (d, 1H), 7.11 (bs, 2H), 5.21 (m, 1H), 4.49 (t, 2H), 4.34 (m, 5H), 4.07-4.16 (m, 3H), 4.01 (t, 2H), 3.72 (t, 2H), 3.60-3.66 (m, 11H), 2.91 (t, 2H), 2.30 (dd, 4H), 1.82 (m, 2H), 1.60 (m, 4H), 1.50 (m, 2H), 1.25 (m, 45H), 1.01 (t, 3H), 0.88 (t, 6H); Positive ES TOF-MS calc for [M+H]$^+$ 1107.7338, found 1107.6374.

Example 3

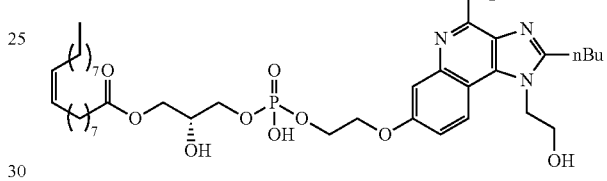

This compound was prepared by following the method of Scheme 5.

Scheme 5

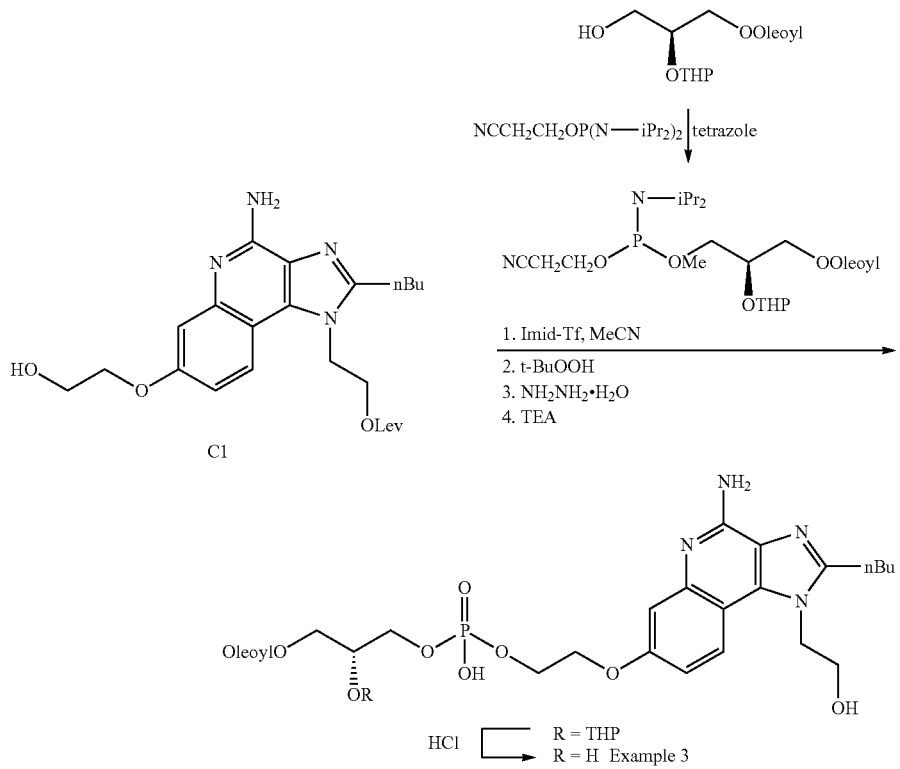

C1 was coupled with 1-palmitoyl-2-tetrahydropyranyl-sn-glycerol following the procedure described in General Procedure 1. After purification by chromatography on silica gel (0 to 10% methanol in chloroform), the corresponding phosphite (I*) was isolated in 34% yield. (I*) was subsequently oxidized with t-butyl peroxide and deprotected sequentially with hydrazine hydrate and TEA as described in General procedure 1 to give the corresponding THP protected intermediate in 85% yield. The THP protecting group was removed by reaction in 1:1 chloroform:methanol (0.02 M) with 4 N HCl/dioxane (2.5 eq) at 0° C. for 3 h. After 3 h, the reaction mixture was dried under vacuum and purified by chromatography on silica gel (0 to 25% methanol/water 95/5 in chloroform) to give Example 3 in 92% yield. $^1$H NMR (400 MHz, CDCl$_3$/CD$_3$OD) δ 7.85 (d, 1H), 7.26 (m, 2H), 5.34 (m, 2H), 4.50 (m, 4H), 4.39 (m, 2H), 4.13 (m, 2H), 4.02 (m, 5H), 2.91 (t, 2H), 2.32 (t, 2H), 2.00 (m, 4H), 1.83 (p, 2H), 1.60 (m, 2H), 1.50 (m, 2H), 1.27 (m, 20H), 1.02 (t, 3H), 0.88 (t, 3H); negative ES TOF-MS calc for [M−H]$^−$ 761.91, found 761.71.

Example 4

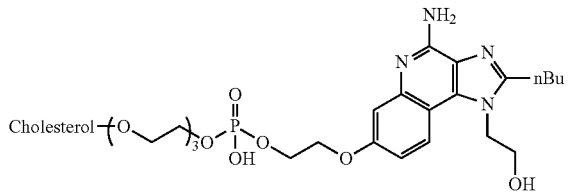

This compound was prepared by following the method of Scheme 6.

Scheme 6

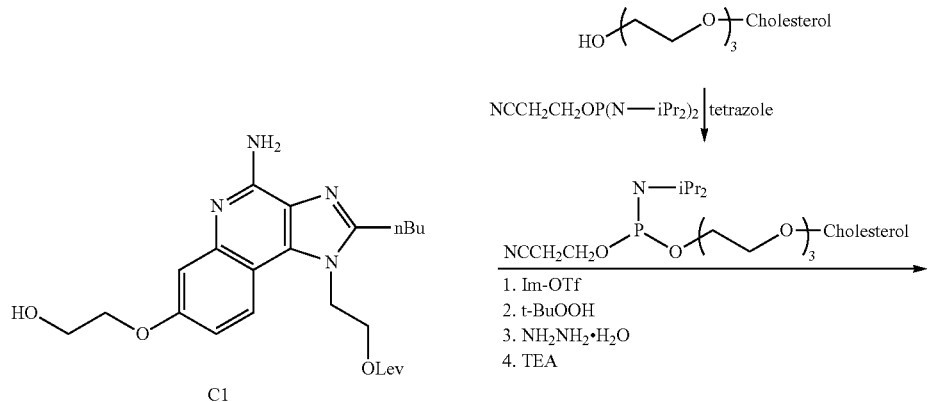

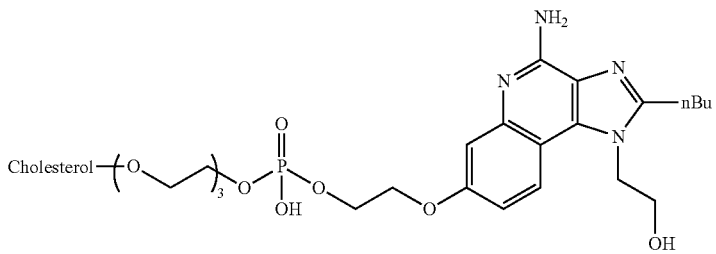

Example 4

C1 was coupled with cholesterol triethyleneglycol following the procedure described in General Procedure 1. After purification by chromatography on silica gel (0 to 10% methanol in chloroform), the corresponding phosphite (I*) was isolated in 37% yield. (I*) was subsequently oxidized with t-butyl peroxide and after purification by chromatography on silica gel (0 to 10% methanol in chloroform), the oxidized phosphite (obtained in 53% yield) was deprotected sequentially with hydrazine hydrate and TEA as described in General procedure 1 to give Example 4 in 71% yield. $^1$H NMR (400 MHz, CDCl$_3$/CD$_3$OD) δ 7.71 (d, 1H), 6.95 (bs, 2H), 5.30 (m, 1H), 4.47 (m, 2H), 4.24 (bs, 4H), 4.07 (m, 2H), 4.02 (m, 2H), 3.71 (t, 2H), 3.63-3.66 (m, 9H contains H$_2$O), 3.15 (m, 1H), 2.91 (t, 2H), 2.33 (dd, 1H), 2.18 (t, 2H), 1.77-2.00 (m, 7H), 1.20-1.68 (m, 20H), 0.81-1.15 (m, 23H), 0.65 (s, 3H); negative ES TOF-MS calc for [M−H]$^−$ 923.5663, found 923.6067.

Example 5

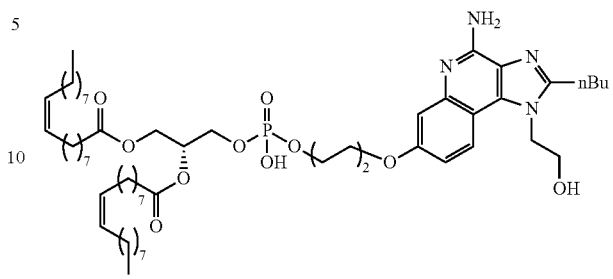

This compound was prepared by following the method of Scheme 7.

Scheme 7

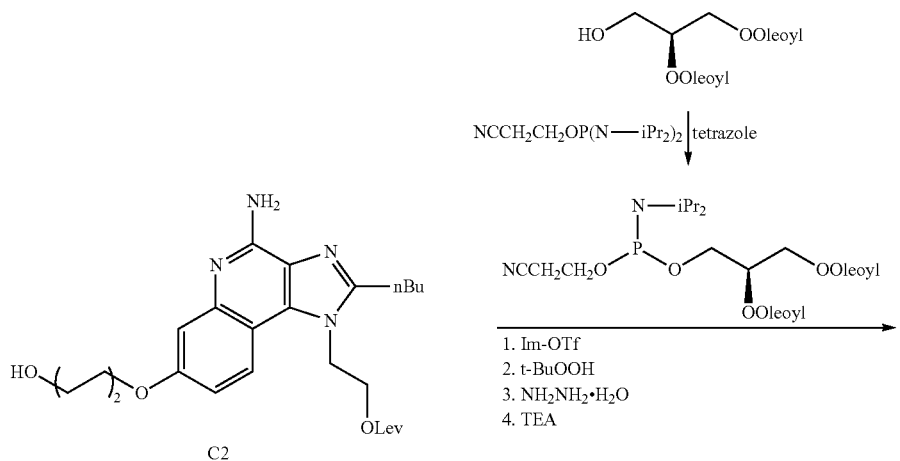

1. Im-OTf
2. t-BuOOH
3. NH$_2$NH$_2$•H$_2$O
4. TEA

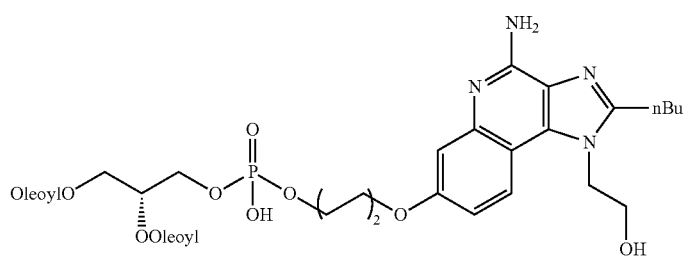

Example 5

C2 was coupled with 1,2-dioleoyl-sn-glycerol following the procedure described in General Procedure 1. After purification by chromatography on silica gel (0 to 10% methanol in chloroform), the corresponding phosphite (I*) was isolated in 74% yield. (I*) was subsequently oxidized with t-butyl peroxide and deprotected sequentially with hydrazine hydrate and TEA as described in General procedure 1 to give Example 5 in 79% yield after chromatography on silica gel (0 to 15% methanol/water 95/5 in chloroform). $^1$H NMR (400 MHz, CDCl$_3$/CD$_3$OD) δ 7.90 (d, 1H), 7.65 (s, 1H), 7.02 (d, 1H), 5.34 (m, 4H), 5.26 (m, 1H), 4.58 (t, 2H), 4.41 (dd, 1H), 4.29 (t, 2H), 4.19 (dd, 1H), 4.1 (m, 4H), 4.00 (t, 2H), 2.98 (t, 2H), 2.30 (m, 4H), 2.00 (m, 10H), 1.89 (m, 2H), 1.80 (m, 2H), 1.58 (m, 4H), 1.51 (m, 2H), 1.29 (m, 40H), 1.03 (t, 3H), 0.88 (m, 6H); negative ES TOF-MS calc for [M−H]$^-$ 1053.7027, found 1053.7857.

Example 6

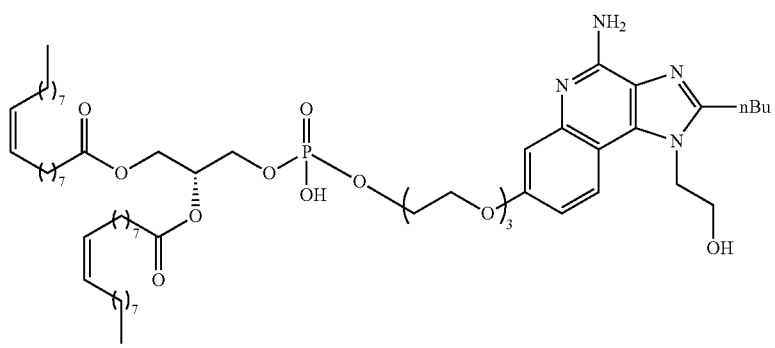

This compound was prepared by following the method of Scheme 8.

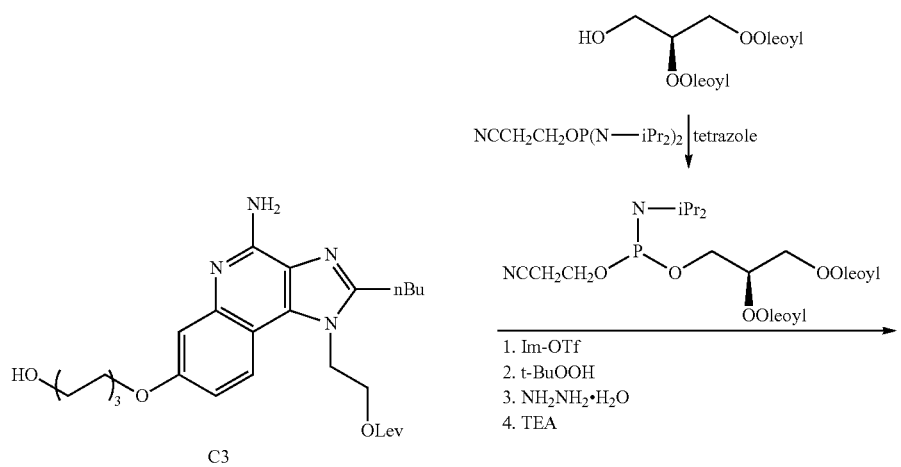

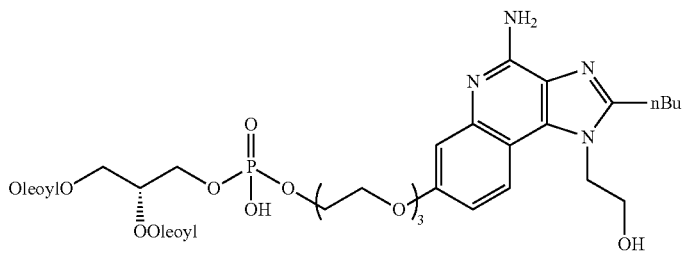

Example 6

C3 was coupled with 1,2-dioleoyl-sn-glycerol following the procedure described in General Procedure 1. After purification by chromatography on silica gel (0 to 10% methanol in chloroform), the corresponding phosphite (I*) was isolated in 75% yield. (I*) was subsequently oxidized with t-butyl peroxide and deprotected sequentially with hydrazine hydrate and TEA as described in General procedure 1 to give Example 6 in 80% yield after chromatography on silica gel (0 to 15% methanol/water 9/1 in chloroform). $^{1}$H NMR (400 MHz, CDCl$_3$/CD$_3$OD) δ 7.91 (d, 1H), 7.47 (s, 1H), 7.07 (d, 1H), 5.34 (m, 4H), 5.27 (m, 1H), 4.58 (t, 2H), 4.42 (dd, 1H), 4.35 (t, 2H), 4.21 (dd, 1H), 4.10 (m, 4H), 4.01 (t, 2H), 3.94 (t, 2H), 3.76 (t, 2H), 3.72 (t, 2H), 3.64 (t, 2H), 2.98 (t, 2H), 2.31 (m, 4H), 2.01 (m, 8H), 1.88 (m, 2H), 1.50 (m, 6H), 1.29 (m, 40H), 1.03 (t, 3H), 0.88 (m, 6H); negative ES TOF-MS calc for [M−H]$^-$ 1113.7232, found 1113.8110.

Example 7

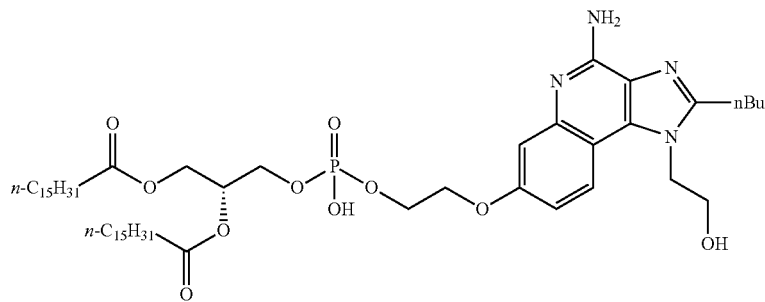

This compound was prepared by following the method of Scheme 9.

Scheme 9

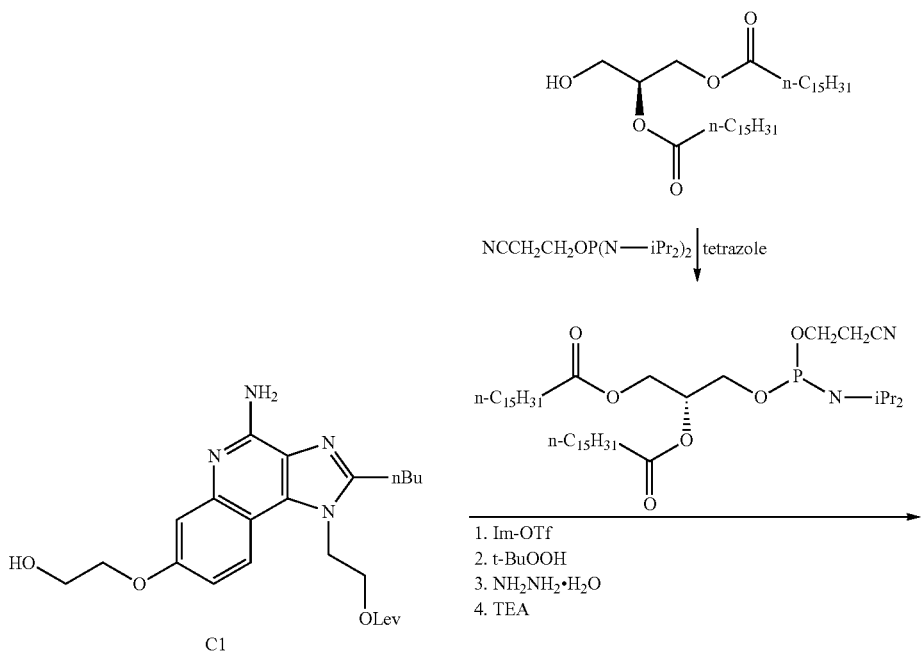

C1 was coupled with 1,2-dipalmitoyl-sn-glycerol following the procedure described in General Procedure 1. After purification by chromatography on silica gel (0 to 12% methanol in chloroform), the corresponding phosphite (I*) was isolated in 67% yield. (I*) was subsequently oxidized with t-butyl peroxide and deprotected sequentially with hydrazine hydrate and TEA as described in General procedure 1 to give Example 7 in 68% yield after purification by chromatography on silica gel (0 to 15% methanol/water 9/1 in chloroform). $^1$H NMR (400 MHz, CDCl$_3$/CD$_3$OD) δ 7.83 (d, 1H), 7.26 (m, 2H), 5.26 (m, 1H), 4.50 (m, 7H), 4.21 (dd, 1H), 4.09 (t, 2H), 4.00 (t, 2H), 2.91 (t, 2H), 2.31 (m, 4H), 1.83 (m, 2H), 1.5 (m, 6H), 1.25 (m, 48H), 1.02 (t, 3H), 0.88 (m, 6H); negative ES TOF-MS calc for [M−H]$^-$ 973.64, found 963.65.

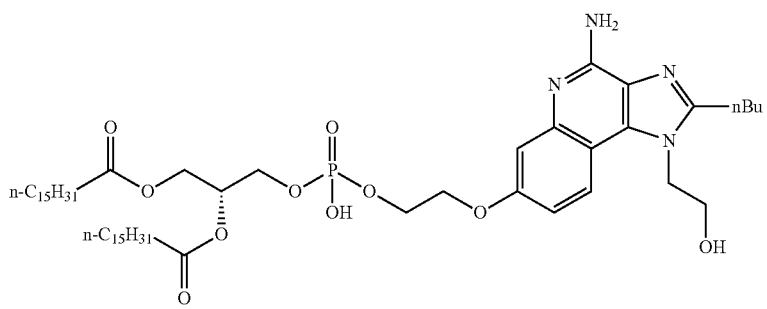

Example 7

Comparative Example 1

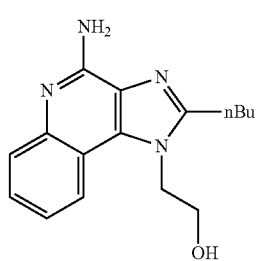

This compound was prepared following known literature procedure (Gerster et al. *J. Med. Chem.*, 2005, 48, 3481).

Comparative Example 2

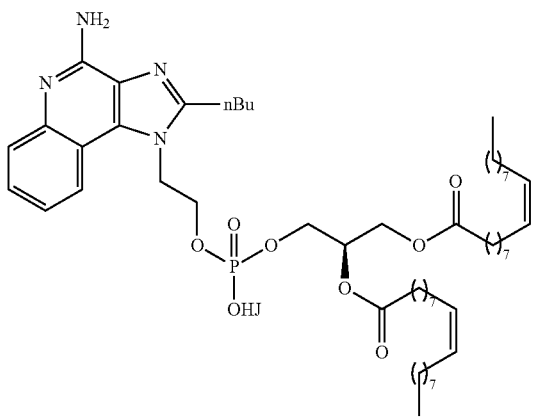

This compound was prepared by following the method of Scheme 10.

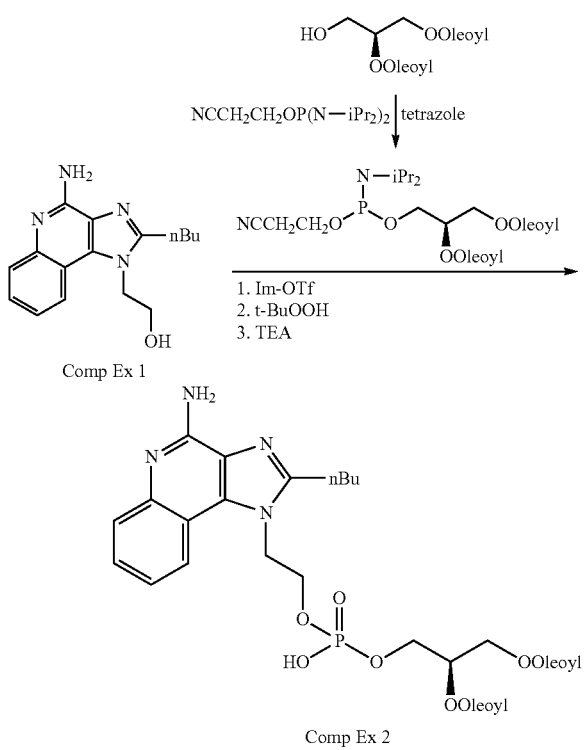

Di-oleoyl-sn-glycerol (2.0 eq) and 2-cyanoethyl N,N,N',N'-tetraisopropylphosphordiamidite (1.5 eq) were dissolved in anhydrous chloroform (0.4 M) at rt. 1H-tetrazole (1.5 eq) was added in four portions over 20 min and the reaction mixture stirred at rt for 2 h. The reaction mixture was cooled to 0° C., Comparative Example 1 (1.0 eq) and imidazolium triflate (2.0 eq) were added, and the reaction mixture allowed to warm up to rt. The reaction was complete after 1 h at rt and the reaction mixture was purified by chromatography on silica gel (0 to 15% methanol in chloroform) to give the corresponding phosphite in 92% yield. The phosphite was dissolved in chloroform (0.07 M) and oxidized by addition of t-butyl hydroperoxide (2.0 eq). After stirring at rt for 30 min, the reaction mixture was concentrated under vacuum. The dried crude was dissolved in acetonitrile (0.08 M). Triethylamine (acetonitrile:TEA 1:0.35 v:v) was added and the reaction mixture stirred at rt for 15 h then dried under vacuum. Purification by chromatography on silica gel (0 to 15% methanol in chloroform) gave Comparative Example 2 in 75% yield. $^1$H NMR (400 MHz, CDCl$_3$/CD$_3$OD) δ 8.18 (bs, 1H), 7.39 (bs, 1H), 7.18 (bs, 1H), 6.92 (bs, 1H), 5.33 (m, 4H), 5.25 (m, 1H), 4.80 (bs, 2H), 4.60 (bs, 2H), 4.41 (dd, J=3.2, 12.0 Hz, 1H), 4.19 (dd, J=6.4, 12.0 Hz, 1H), 4.03 (t, J=6.0 Hz, 2H), 3.01 (bs, 2H), 2.30 (m, 4H), 1.98 (m, 4H), 1.57 (m, 6H), 1.27 (m, 40H), 1.05 (t, J=7.2, 3H), 0.88 (m, 6H); negative ES TOF-MS calc for [M−H]$^-$ 965.6497, found 965.6498.

Comparative Example 3

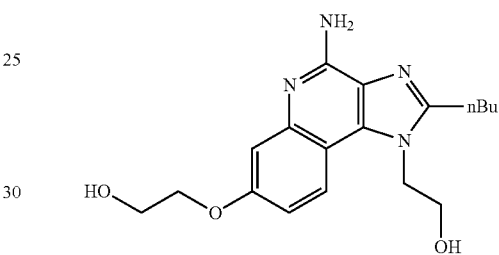

This compound was prepared by following the method of Scheme 11.

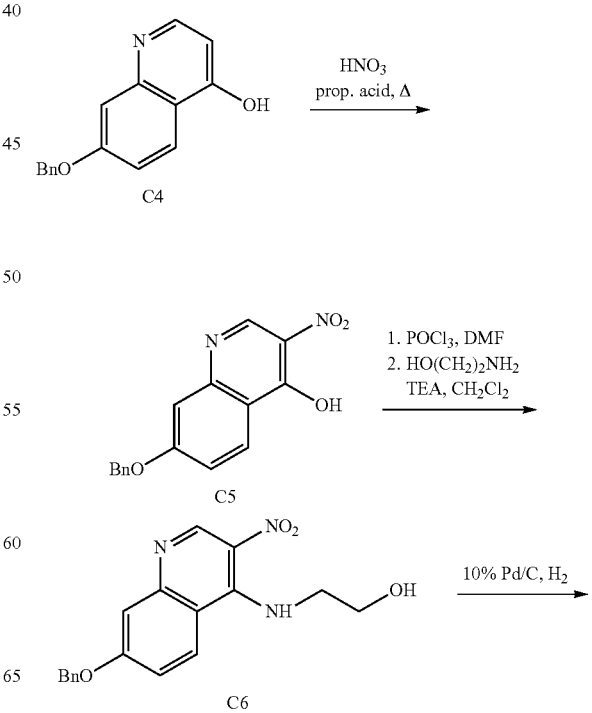

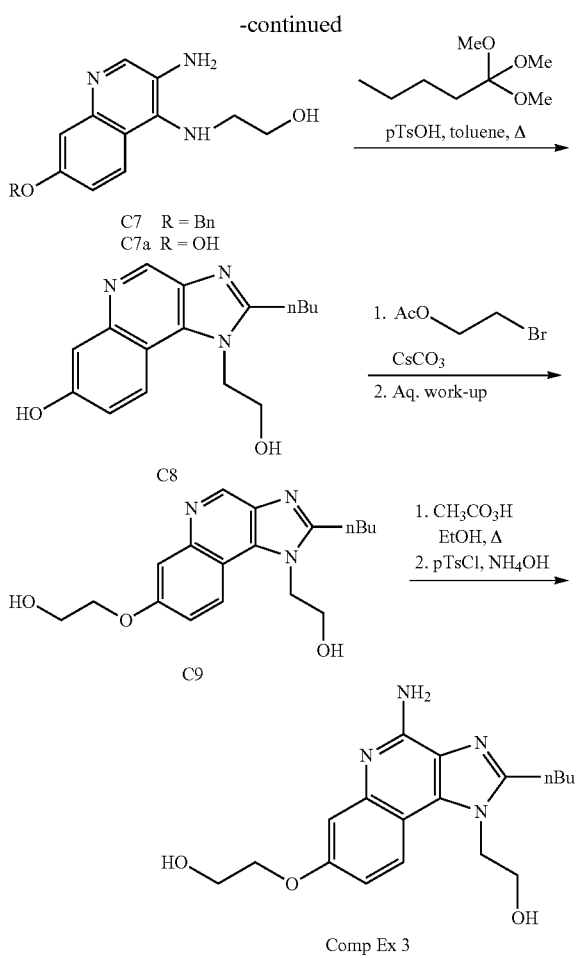

Concentrated nitric acid (70% content, 1.5 eq) was very slowly added to a solution of C4 in propionic acid (0.37 M) heated to 125° C. The reaction mixture was stirred 3 h at 125° C., allowed to cool to rt and filtered on filter paper. The collected solid was rinsed with water and dried under vacuum to give C5 in 74% yield.

A solution of POCl$_3$ (1.2 eq) in DMF (1.6 M), prepared by dropwise addition of POCl$_3$ to cold (0° C.) DMF and stirring for 30 min at 0° C., was slowly added to a suspension of C5 in DMF (0.45 M). At the end of the addition, the reaction mixture was heated to 100° C. for 5 min, cooled to rt and poured into ice water. The resulting precipitate was filtered and dried under vacuum overnight. The dried solid was dissolved in chloroform (0.4 M) and TEA (1.4 eq) and ethanolamine (1.2 eq) were added and the reaction mixture stirred at 40° C. for 1 h then at rt for 4 h. The reaction mixture was concentrated under vacuum, and the dried solid washed with water, filtered, dried, triturated with hot ethyl acetate to give C6 in 94% yield. $^1$H NMR (400 MHz, CD$_3$OD) δ 9.31 (s, 1H), 8.22 (d, 1H), 7.3 (m, 6H), 7.17 (dd, 1H), 5.23 (s, 2H), 4.05 (t, 2H), 3.85 (t, 2H). C6 was dissolved in 1:1 solution of chloroform:methanol (0.01 M) and hydrogenated with 10% Pd/C using a ThalesNano H-Cube (full H$_2$, 40-60° C.). The hydrogenated solution was concentrated, dried under vacuum and purified by chromatography on silica gel to give C7 and C7a in 21% and 41% yield, respectively. C7: LC-MS [M+H]$^+$ 310.13; C7a: LC-MS [M+H]$^+$ 220.08.

p-TsOH (0.2 eq) was added to a suspension of C7a in toluene (0.15 M) and the suspension heated to 60° C. Trimethylorthovalerate (2 eq) was dropwise added and the mixture stirred at 60° C. for 5 h. After cooling to rt, the reaction mixture was concentrated, dried under vacuum and purified by chromatography on silica gel (5 to 40% methanol in chloroform). Fractions containing the desired product were dried and recrystallized from chloroform/methanol/ethyl acetate to give C8 in 42% yield.

Cesium carbonate (3 eq) was added to a solution of C8 in DMF (0.18 M) at 0° C., A solution of acetyl protected bromoethanol in DMF (1.2 eq, 1.3 M) was then added dropwise and the reaction mixture stirred at 0° C. for 10 min then allowed to warm up to rt. After stirring overnight at rt and aqueous work-up, the dried crude was purified by chromatography on silica gel (0 to 15% methanol in chloroform) to give C9 in 77% yield.

Peracetic acid (1.2 eq) was added to a suspension of C9 in reagent ethanol (0.08 M) and the reaction mixture heated to 60° C. for 2.5 h. Additional peracetic acid (0.1 eq) was added and the reaction mixture heated to 60° C. for another 6 h. After concentration and drying under vacuum, the crude was purified by chromatography on silica gel (0 to 35% methanol in chloroform) to give the corresponding N-oxide intermediate in 73% yield. p-TsCl (1.1 eq) was slowly added to a suspension of N-oxide in aqueous concentrated ammonia (0.3 M) and the reaction mixture stirred at rt for 30 min. More p-TsCl (0.9) was added and after 30 min at rt, the reaction mixture was quenched with water. After aqueous work-up, the crude was purified by chromatography on silica gel (0 to 25% methanol in chloroform) to give Comparative Example 3 as an off-white solid in 46% yield. $^1$H NMR (400 MHz, CD$_3$OD) δ 8.25 (d, 1H), 7.28 (m, 2H), 4.78 (t, 2H), 4.21 (t, 2H), 4.03 (t, 2H), 3.95 (t, 2H), 3.16 (t, 2H), 1.98 (m, 2H), 1.56 (m, 2H), 1.05 (t, 3H); Positive ES TOF-MS calc for [M+H]$^+$ 345.1927, found 345.2241.

Comparative Example 4

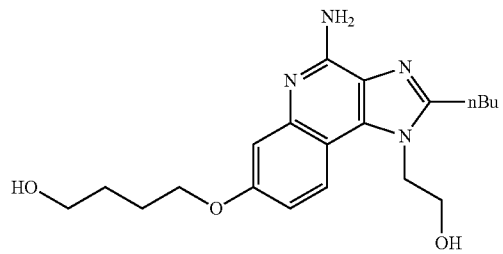

This compound was prepared by following the method of Scheme 12.

Scheme 12

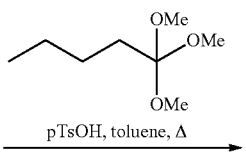

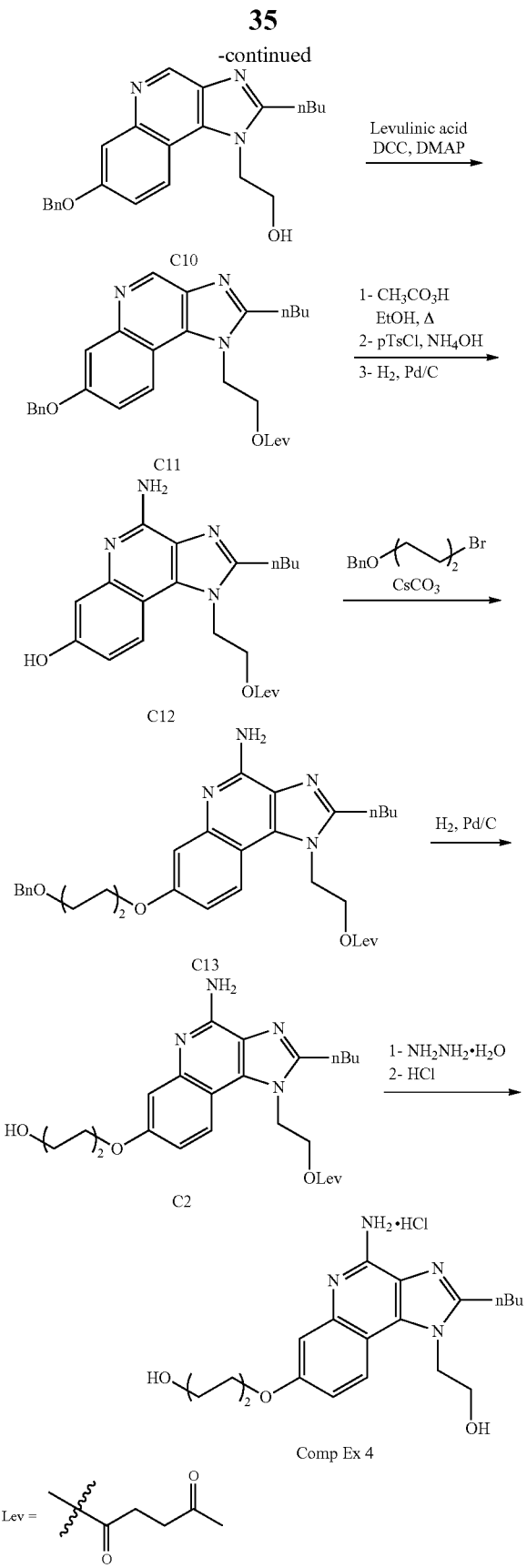

Trimethylorthovalerate (2 eq) was dropwise added and the mixture stirred at 60° C. for 5 h. More trimethylorthovalerate was added as needed to push the reaction to completion. After cooling to rt, the reaction mixture was filtered, the precipitate washed with ethyl acetate and dried to give C10 as a light brown solid in 97% yield.

Levulininc acid (1.2 eq) was added to a suspension of C10 in anhydrous methylene chloride (0.27 M). The reaction mixture was cooled to 0° C. and DMAP (0.02 eq) and DCC (1.05 eq) were added. After 10 min at 0° C. followed by 40 min at rt, the reaction mixture was adsorbed on silica gel and purified by chromatography on silica gel (0 to 8% methanol in chloroform) to give C11 in 66% yield.

Peracetic acid (1.2 eq) was added to a suspension of C11 in reagent ethanol (0.16 M) and the reaction mixture heated to 60° C. for 3 h. After concentration and drying under vacuum, the crude was triturated with hot ethyl acetate, filtered and dried to give the corresponding N-oxide intermediate in 83% yield. Aqueous ammonia (1:3 ammonia:methylene chloride) was added to a solution of N-oxide in methylene chloride (0.2 M). p-TsCl (1.1 eq) was slowly added and the reaction mixture stirred at rt for 30 min then quenched with water. After aqueous work-up, the dried crude dissolved in 1:1 chloroform:methanol was hydrogenated on 10% Pd/C using a ThalesNano H-Cube (60° C., full $H_2$ mode). The hydrogenated solution was concentrated, dried under vacuum, and purified by chromatography on silica gel (0 to 15% methanol in chloroform) to give C12 in 88% yield. Cesium carbonate (3 eq) was added to a solution of C12 in DMF (0.2 M) at 0° C., A solution of TBS protected bromobutanol in DMF (1.2 eq, 1.3 M) was then added dropwise and the reaction mixture stirred at 0° C. for 10 min then at rt for 7 h then quenched with water. After aqueous work-up, the dried crude was purified by chromatography on silica gel (0 to 10% methanol in chloroform) to give C13 in 78% yield.

A solution of C13 in 1:1 chloroform:methanol (0.016 M) was hydrogenated on 10% Pd/C using a ThalesNano H-Cube (rt, full $H_2$ mode). The hydrogenated solution was concentrated, dried under vacuum, and purified by chromatography on silica gel (0 to 15% methanol in chloroform) to give C14 in 66% yield. A solution of C14 in a 4:1 mixture of pyridine:acetic acid (0.05M) was reacted with hydrazine hydrate (5.0 eq). After 5-10 min at rt, the reaction mixture was cooled to 0° C. and stirred with 2,4-pentanedione (10.0 eq) at 0° C. for 5 min. After aqueous work-up, the dried solid was salted with concentrated HCl and recrystallized from methanol/ethyl acetate to give Comparative Example 4 in 78% yield. $^1$H NMR (400 MHz, $CD_3OD$) δ 8.20 (d, 1H), 7.21 (m, 2H), 4.70 (t, 2H), 4.17 (t, 2H), 4.01 (t, 2H), 3.65 (t, 2H), 3.05 (t, 2H), 1.93 (m, 4H), 1.75 (m, 2H), 1.54 (hex, 2H), 1.04 (t, 3H), Positive ES TOF-MS calc for $[M+H]^+$ 345.1927, found 345.2241.

Comparative Example 5

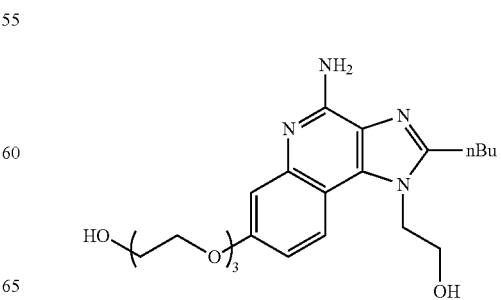

p-TsOH (0.2 eq) was added to a suspension of C7 in toluene (0.15 M) and the suspension heated to 60° C.

This compound was prepared by following the method of Scheme 13.

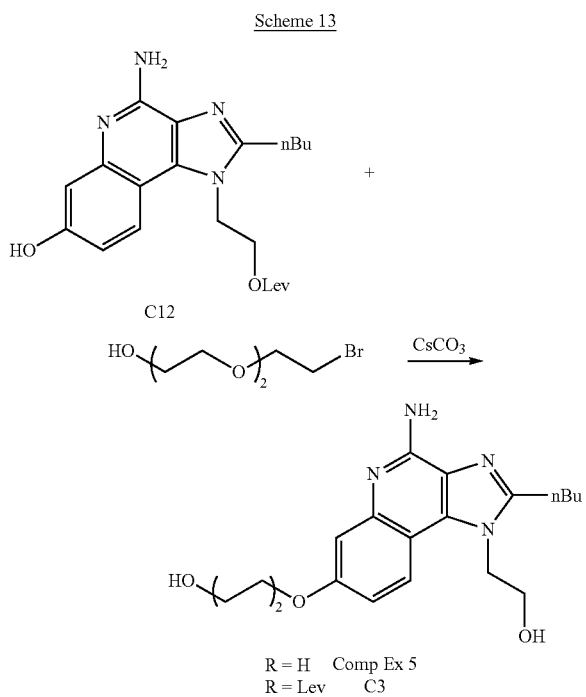

Cesium carbonate (3 eq) was added to a solution of C12 in DMF (0.1 M) at 0° C., A solution of triethyleneglycol bromide in DMF (1.2 eq, 1.3 M) was then added dropwise and the reaction mixture stirred at 0° C. for 10 min then at rt for 17 h then quenched with water. After aqueous work-up, the dried crude was purified by chromatography on silica gel (0 to 30% methanol in chloroform) to give Comparative Example 5 in 13% yield. $^1$H NMR (400 MHz, CD$_3$OD) δ 8.20 (d, 1H), 7.21 (m, 2H), 4.70 (t, 2H), 4.17 (t, 2H), 4.01 (t, 2H), 3.65 (t, 2H), 3.05 (t, 2H), 1.93 (m, 4H), 1.75 (m, 2H), 1.54 (hex, 2H), 1.04 (t, 3H); Positive ES TOF-MS calc for [M+H]$^+$ 433.2451, found 433.2816.

Intermediate C1

This compound was prepared by following the method of Scheme 14.

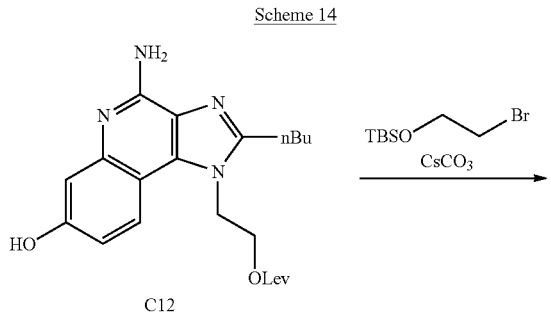

Cesium carbonate (6 eq) was added to a solution of C12 in DMF (0.11 M) at 0° C., A solution of TBS protected bromoethanol in DMF (1.2 eq, 0.4 M) was then added dropwise and the reaction mixture stirred at 0° C. for 10 min then allowed to warm up to rt. After stirring at rt or 5 h and aqueous work-up, the dried crude was purified by chromatography on silica gel (0 to 5% methanol in chloroform) to give C14 in 59% yield. LC-MS: [M+H]$^+$ 557.3.

20 eq of TFA were added to a solution of C14 in methylene chloride (0.18M) and the reaction mixture stirred at rt for 4 h. After drying under vacuum and purification by chromatography on silica gel (0 to 20% methanol in chloroform), C1 (TFA salt) was obtained in 83% yield.

Aqueous Formulations

I. Salt Screening

To improve the solubility of the lipidated imidazoquinoline derivatives (IQs) described herein, a salt screening study was performed. For this study, acid salts tested included naphthalene-1,5-disulfonic acid; benzenesulfonic acid; HCl; and 2-naphthalenesulfonic acid. Basic salts tested included choline bicarbonate, choline hydroxide, TRIS; Ethylene diamine; and N-methylglucamine.

With the exception of choline salts, none of the salts tested had a significant effect on solubility of the IQ compound. In addition, LCMS revealed that choline salt forms of IQ generally exhibited less degradation during the drying process than the other salts tested. Based on the salt screening results, choline bicarbonate and chlorine hydroxide salts were selected for further formulation process development.

II. Choline Salting Methods

During the salt screening experiments described above, it was observed that the solvent removal steps could impair recovery of the salted IQ compound. Specifically, increased drying times resulted in lower solubility and increased degradation of the IQ compound. It was surprisingly discovered that acceptable solubility and stability can be achieved by either avoiding the use of organic solvents (Direct Aqueous Salting Method), or decreasing the drying time required to remove the solvent (Dry Salting Method).

FIG. 18 is a schematic representation of the prior art salting method (A), and the two novel salting methods (B—Direct Aqueous method; C—Dry Salting method).

A. Initial Salting Method

IQ compound salts were prepared according to methods known in the art. Briefly, lipidated imidazoquinoline derivatives (IQ) are dissolved in tetrahydrofuran (THF). Acid or base salts are dissolved in methanol, and added to the dissolved IQ. Solvents are then removed by evaporation using a rotary evaporator, followed by additional drying under high vacuum at room temperature for 1-19.5 hours. After solvent evaporation, a 2% glycerol in water solution is added to the salted compound and sonicated for 15 minutes with a probe sonicator. The salted formulation is then sterile filtered with a 0.22 um syringe filter. Concentration of the IQ salts is determined by RP-HPLC, and product identity is confirmed by liquid chromatography-mass spectrometry (LCMS).

B. Direct Aqueous Salting Method

Salts of the compounds of Examples 1-7 were prepared according to the following methods. First, the lipidated imidazoquinoline derivative (IQ) was dissolved directly in an aqueous vehicle (2% glycerol in water). A choline salt, either choline bicarbonate or choline hydroxide, was added directly to the dissolved IQ compound in amounts of 0.6, 0.8, 1 and 1.2 molar equivalents (EQ). The solution was then sonicated for 15-90 minutes with a probe sonicator at a temperature of 60-80° C. The salted formulation was sterile filtered with a 0.22 um syringe filter.

Choline salts of the compounds of Examples 1-7 were at least as soluble as compounds prepared by the prior art salting procedure, but surprisingly had significantly less degradation than IQ salts prepared by the prior art method. Furthermore, the direct aqueous process can be carried out in less time than the prior art method, and avoids the use of organic solvents. Similar results were observed for salted compounds made with 0.6, 0.8 and 1.2 EQ choline salts. These results indicate that direct aqueous salting is an advantageous method for use with the IQ compounds described herein.

C. Dry Salting Method

Salts of the compounds of Examples 1-7 were prepared according to the following methods. First, the lipidated imidazoquinoline derivative (IQ) was dissolved in tetrahydrofuran (THF). A choline salt, either choline bicarbonate or choline hydroxide, was added directly to the dissolved IQ compound in amounts up to 4 molar equivalents (EQ). The THF solvent was then removed by evaporation using a rotary evaporator. Vacuum drying was not performed. After solvent evaporation, a 2% glycerol in water solution was added to the salted compound and sonicated for 15 minutes with a probe sonicator. The salted formulation was then sterile filtered with a 0.22 um syringe filter.

Choline bicarbonate and choline hydroxide salts of the compounds of Examples 1-7 were found to exhibit better solubility and stability as compared to the unsalted formulation, indicating that the dry salting method is an advantageous method for use with the IQ compounds described herein.

Biological Data

Methods

Assay for hTLR7 and hTLR8 Agonist Activity in HEK-293 Cells

Determination of TLR agonist activity was performed using the HEK293 binding assay. This assay measures TLR7 and TLR8 selectivity and potency of the compounds tested. HEK293 cells expressing human TLR7 or TLR8 and NFκB responsive Secreted Embryonic Alkaline Phosphatase (SEAP) reporter gene were obtained from InvivoGen (San Diego, Calif.). These cells were maintained in culture media of Dulbecco's Modified Eagle Medium (DMEM) (Invitrogen, Grand Island, N.Y.), 10% Fetal Bovine Serum (FBS) (Sigma, St. Louis, Mo.) and selection antibiotics (Invitrogen, and Invivogen). HEK293 stably transfected with human TLR7 (hTLR7) or human TLR8 (hTLR8) were stimulated for 24 h with aqueous formulations of test compounds and culture supernatants were analyzed for NFκB activation using the colorimetric SEAP detection kit QuantBlue (InvivoGen).

Assays to Measure Cytokine Induction

Test compounds were evaluated for cytokine induction in human peripheral blood mononuclear cells (hPBMCs).

Preparation of hPBMCs

Primary human PBMCs were isolated from fresh blood from healthy donors via Ficoll gradient separation and plated at $0.5 \times 10^6$ cells/well in 96-well tissue culture plates (RPMI-1640 plus 10% FBS). hPBMCs were maintained with RPMI-1640 culture media (Invitrogen, Grand Island, N.Y.), antibiotics (Invitrogen) and 10% FBS (Sigma).

Incubation and Assays for IFN-γ, IFN-α and TNF-α hPBMCs were stimulated for 24 h with aqueous formulations of test compounds. Culture supernatants were analyzed for TNF-α and IFN-γ induction using multiplex kits (FluoroKine multiplex kits from R&D Systems, Minneapolis, Minn.) and for IFN-α induction using human IFN-α VeriKine ELISA kit (Pestka Biomedical Laboratories, Inc., Piscataway, N.J.).

Results

Figure 2:
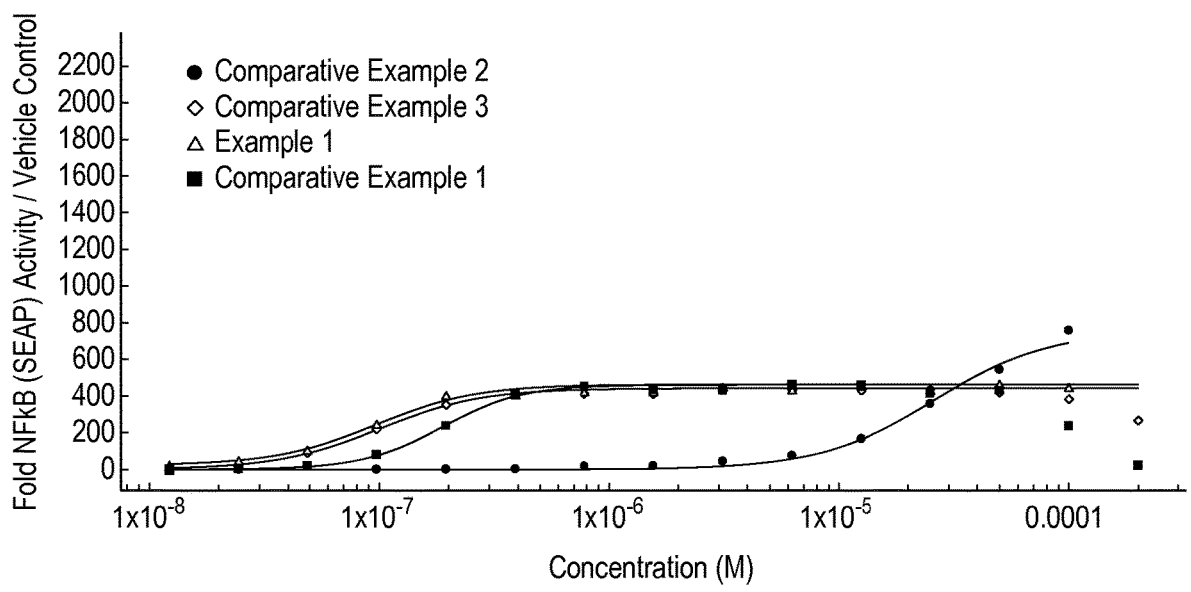
FIG. 2 shows a plot of curves of various compounds tested in the hTLR8 agonist reporter assay in HEK293 cells.

Comparative Examples 1, 2 and 3 and Example 1 were tested for their hTLR7 and hTLR8 agonist activity and the results are shown in FIGS. 1 and 2 and summarised in Table 1 below.

TABLE 1

|  | Comp Ex 1 | Comp Ex 2 | Comp Ex 3 | Ex 1 |
| --- | --- | --- | --- | --- |
| hTLR7 ED50 (µM) | 0.58 | 34.58 | 1.56 | 1.06 |
| hTLR8 ED50 (µM) | 0.19 | 25.99 | 0.10 | 0.10 |
| hTLR7/8 ratio | 3.1 | 1.3 | 15.5 | 11.0 |

The results show that Example 1 demonstrates notable selectivity for hTLR8/hTLR7 and is significantly more potent as an agonist of hTLR7 and hTLR8 than Comparative Example 2 in this reporter assay.

Figure 3:
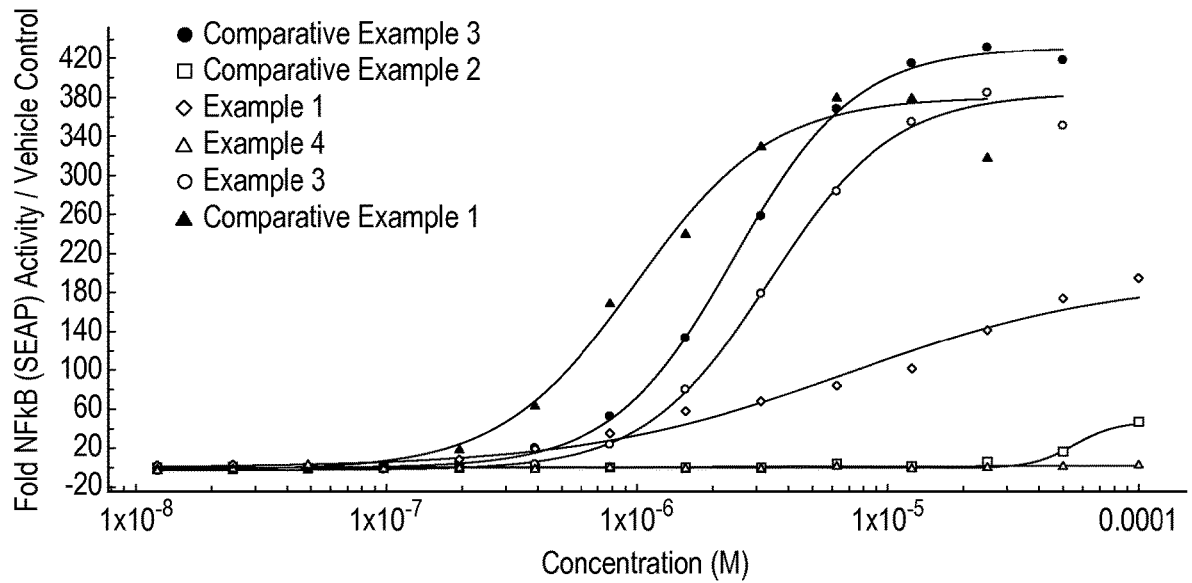
FIG. 3 shows a plot of curves of various compounds tested in the hTLR7 agonist reporter assay in HEK293 cells.
Figure 4:
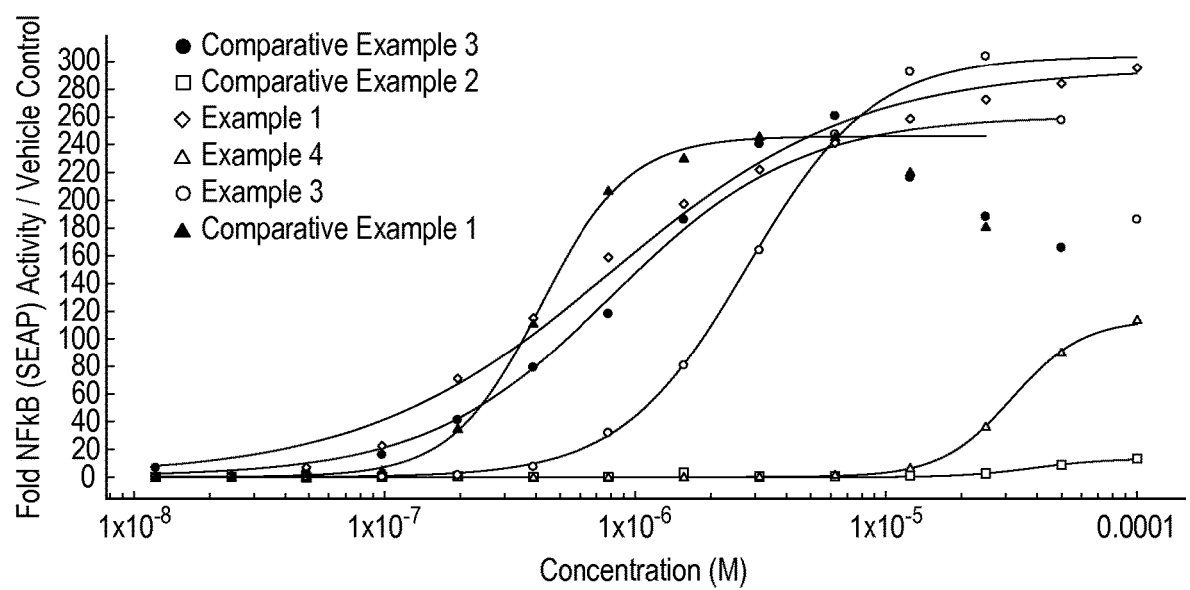
FIG. 4 shows a plot of curves of various compounds tested in the hTLR8 agonist reporter assay in HEK293 cells.

On another occasion, Comparative Examples 1, 2 and 3 and Examples 1, 3 and 4 were tested for their hTLR7 and hTLR8 agonist activity and the results are shown in FIGS. 3 and 4 and summarised in Table 2 below.

TABLE 2

|  | Comp Ex 1 | Comp Ex 2 | Comp Ex 3 | Ex 1 | Ex 3 | Ex 4 |
| --- | --- | --- | --- | --- | --- | --- |
| hTLR7 ED50 (µM) | 1.0 | 55.4* | 2.4 | 7.0 | 3.4 | — |
| hTLR8 ED50 (µM) | 0.4 | 39.2* | 0.8 | 0.8 | 2.8 | 31.9 |
| hTLR7/8 ratio | 2.3 | 1.4 | 2.9 | 8.9 | 1.2 | — |

*only very low levels of NF$_K$B activation were detected

The results confirm that Example 1 is more active than Comparative Example 2 as an agonist of hTLR7 and hTLR8. Example 3 is also a potent agonist of hTLR7 and hTLR8, being approximately equally potent at both receptors in this reporter assay. Example 4 was a weaker agonist of hTLR8 and did not agonise hTLR7 in this reporter assay.

Figure 5:
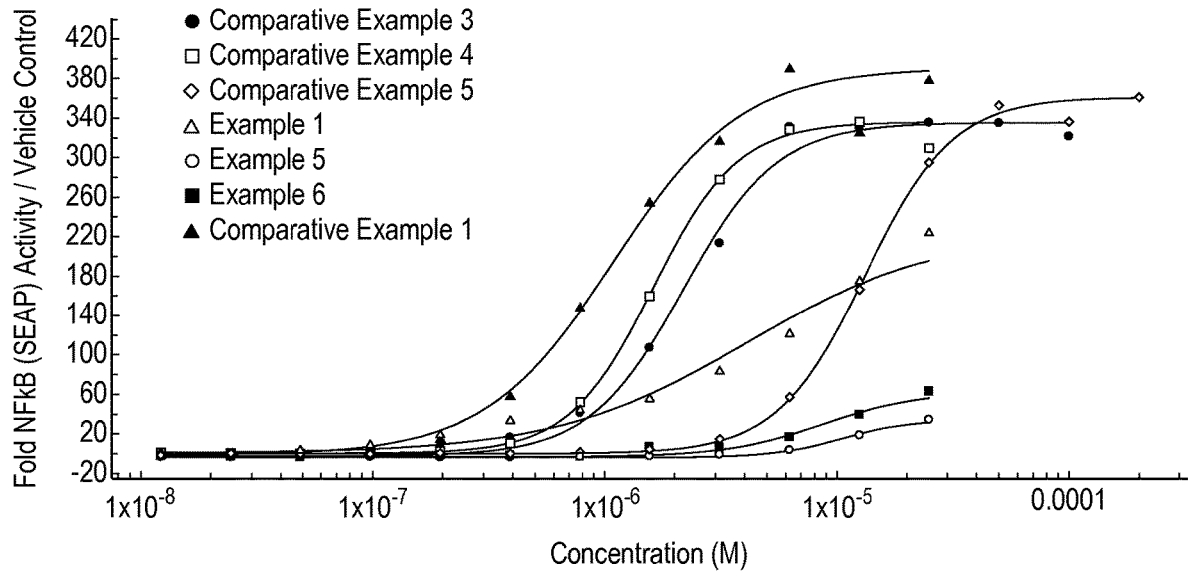
FIG. 5 shows a plot of curves of various compounds tested in the hTLR7 agonist reporter assay in HEK293 cells.
Figure 6:
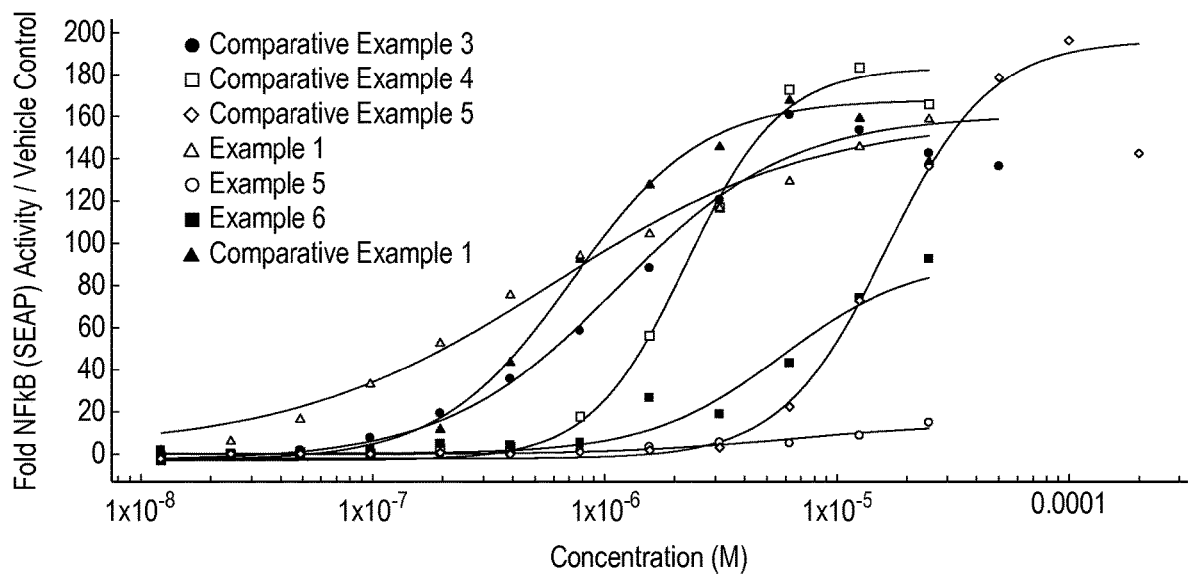
FIG. 6 shows a plot of curves of various compounds tested in the hTLR8 agonist reporter assay in HEK293 cells.

On another occasion, Comparative Examples 1, 3, 4 and 5 and Examples 1, 5, and 6 were tested for their hTLR7 and hTLR8 agonist activity and the results are shown in FIGS. 5 and 6 and summarised in Table 3 below.

TABLE 3

|  | Comp Ex 1 | Comp Ex 3 | Comp Ex 4 | Comp Ex 5 | Ex 1 | Ex 5 | Ex 6 |
|---|---|---|---|---|---|---|---|
| hTLR7 ED50 ($\mu$M) | 1.1 | 2.2 | 1.6 | 13.2 | 4.1 | 10.5* | 8.7* |
| hTLR8 ED50 ($\mu$M) | 0.72 | 1.1 | 2.2 | 16.3 | 0.59 | 6.6* | 5.8 |
| hTLR7/8 ratio | 1.5 | 1.9 | 0.7 | 0.8 | 6.9 | 1.6 | 1.5 |

*only very low levels of NF$_K$B activation were detected

The results confirm that Example 1 is an agonist of both TLR7 and TLR8.

Example 5 was a very weak agonist of hTLR7 or hTLR8 in this reporter assay. Comparative Example 4 was a good agonist of hTLR7 and hTLR8 but Comparative Example 5 was a quite weak agonist of hTLR7 and hTLR8 in this reporter assay. Example 6 was a reasonably potent agonist of hTLR8 in this reporter assay but was a very weak agonist of hTLR7 in this reporter assay.

Figure 7:
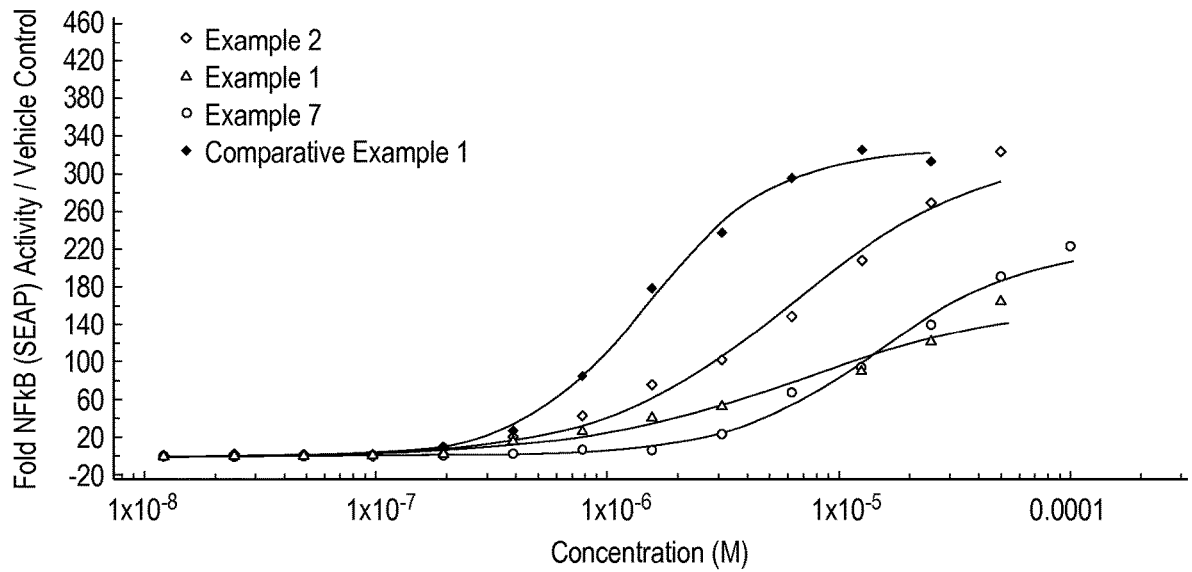
FIG. 7 shows a plot of curves of various compounds tested in the hTLR7 agonist reporter assay in HEK293 cells.
Figure 8:
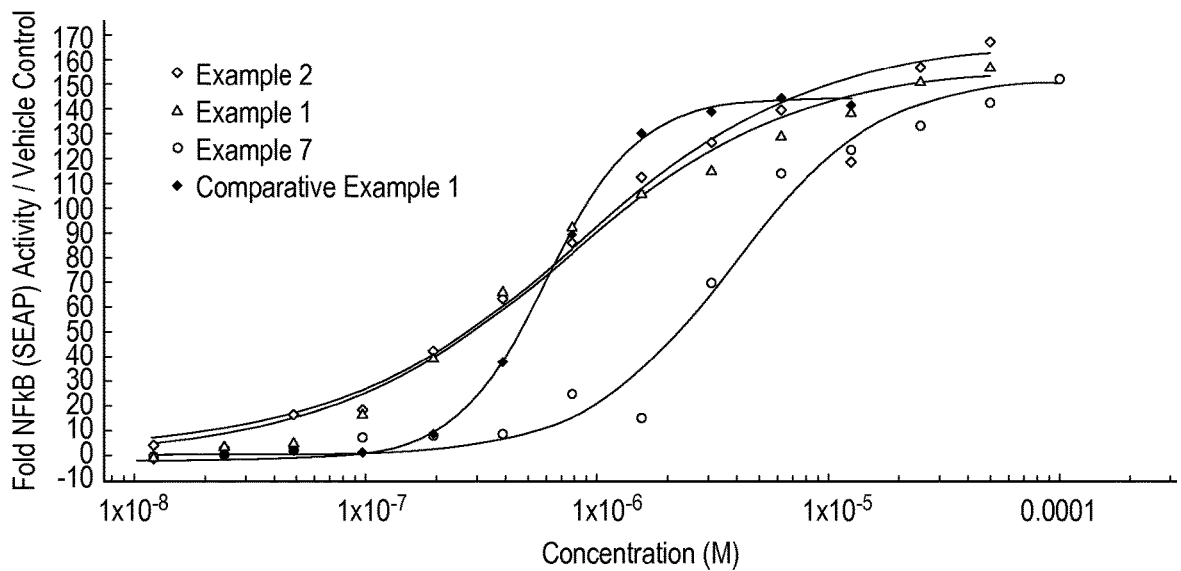
FIG. 8 shows a plot of curves of various compounds tested in the hTLR8 agonist reporter assay in HEK293 cells.

On another occasion, Comparative Example 1 and Examples 1, 2, and 7 were tested for their TLR7 and TLR8 agonist activity and the results are shown in FIGS. 7 and 8 and summarised in Table 4 below.

TABLE 4

|  | Comp Ex 1 | Ex 1 | Ex 2 | Ex 7 |
|---|---|---|---|---|
| hTLR7 ED50 ($\mu$M) | 1.5 | 7.0 | 6.1 | 14.6 |
| hTLR8 ED50 ($\mu$M) | 0.61 | 0.71 | 0.81 | 3.81 |
| hTLR7/8 ratio | 2.4 | 9.9 | 7.5 | 3.8 |

The results for Example 1 were similar to those presented in Table 1, 2 and 3 above. Example 2 showed a similar profile to that of Example 1 in that it was significantly more potent as an agonist of hTLR8 than hTLR7. Example 7 was also an agonist of hTLR7 and hTLR8 but less potent than Examples 1 and 2, particularly at hTLR8.

Figure 9:
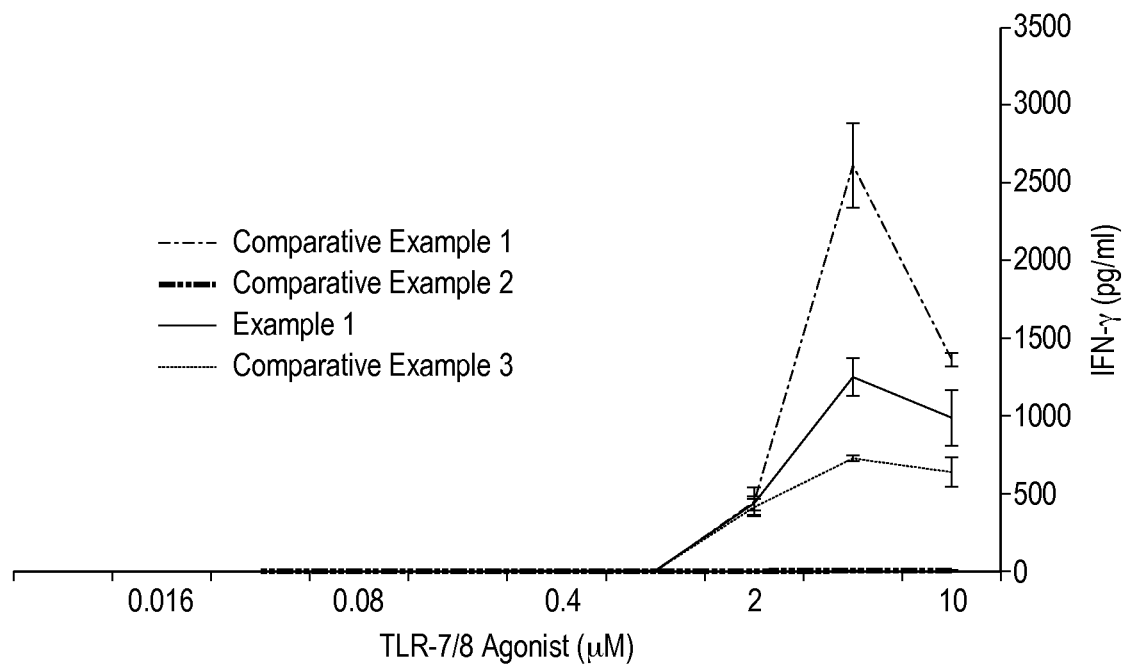
FIG. 9 shows a plot of curves of various compounds tested in the assay for IFN-γ induction in hPBMCs.
Figure 10:
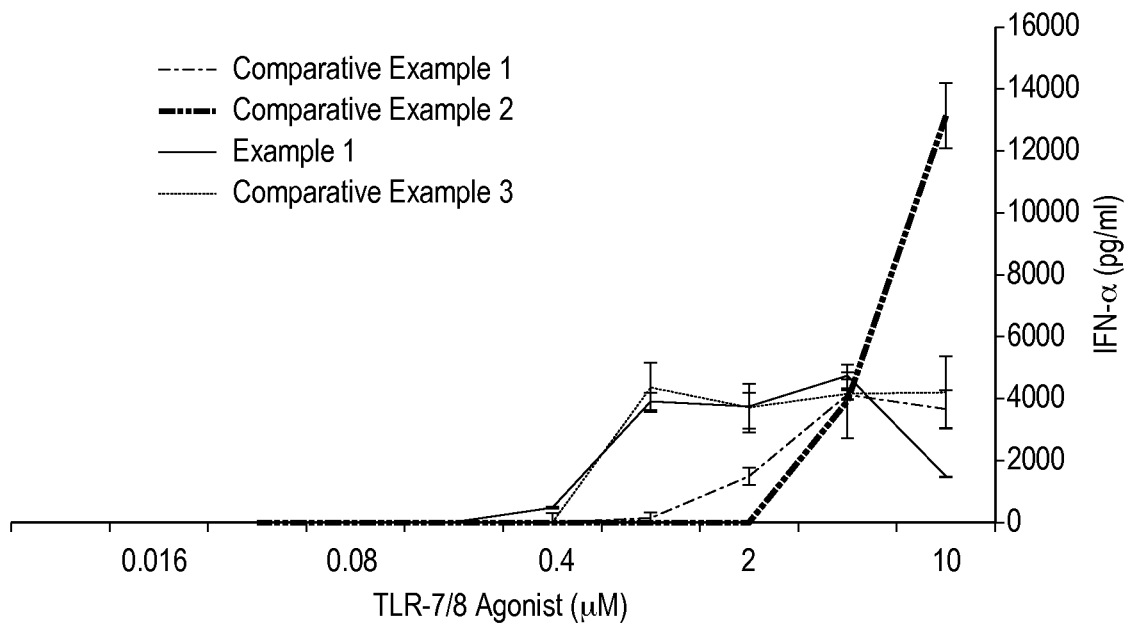
FIG. 10 shows a plot of curves of various compounds tested in the assay for IFN-α induction in hPBMCs

Comparative Examples 1, 2 and 3 and Example 1 were tested for their activity in inducing IFN-$\gamma$ and IFN-$\alpha$ in hPBMCs and the results are shown in FIGS. 9 and 10.

Example 1 was more potent than Comparative Example 3 but less potent than Comparative Example 1 at inducing IFN-$\gamma$ but in this assay. Comparative Example 2 did not induce any IFN-$\gamma$ in this assay.

Example 1 and Comparative Example 3 were equipotent at inducing IFN-$\alpha$ and these were more potent than Comparative Example 1 and Comparative Example 2 in this assay at a lower dose.

Figure 11:
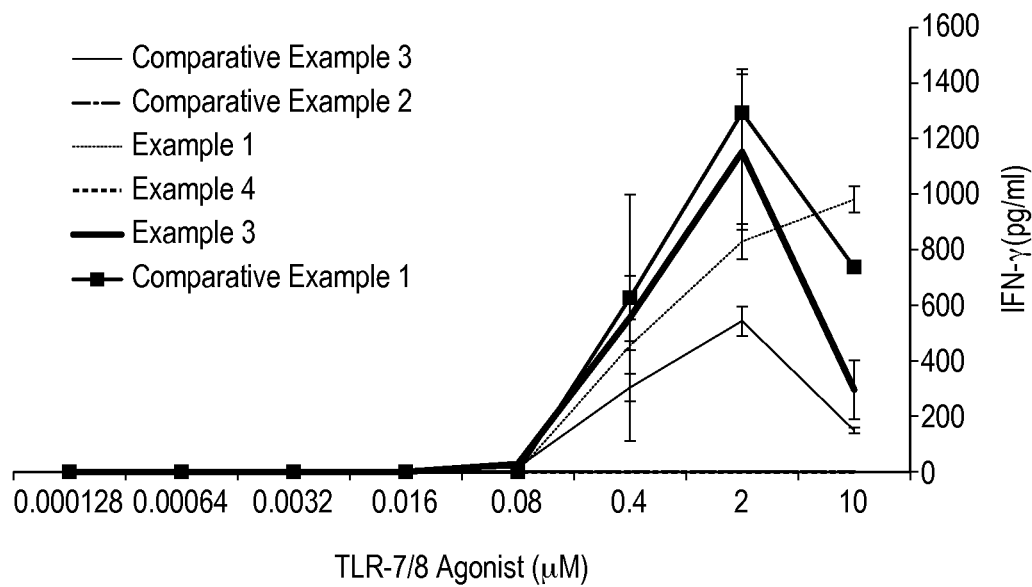
FIG. 11 shows a plot of curves of various compounds tested in the assay for IFN-γ induction in hPBMCs.
Figure 12:
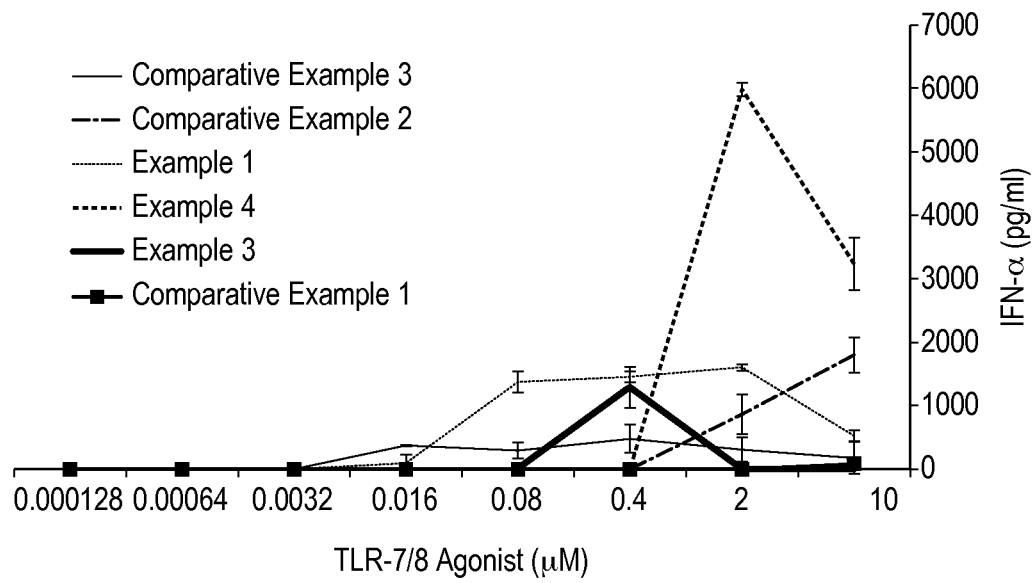
FIG. 12 shows a plot of curves of various compounds tested in the assay for IFN-α induction in hPBMCs
Figure 13:
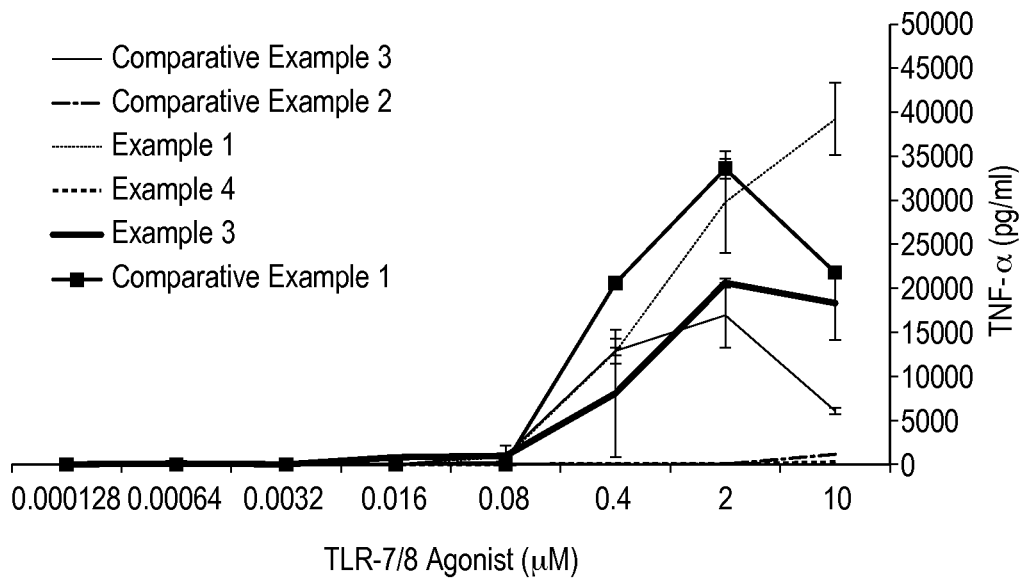
FIG. 13 shows a plot of curves of various compounds tested in the assay for TNF-α induction in hPBMCs

On another occasion Comparative Examples 1, 2 and 3 and Examples 1, 3 and 4 were tested for their activity in inducing IFN-$\gamma$, IFN-$\alpha$ and TNF-$\alpha$ in hPBMCs and the results are shown in FIGS. 11, 12 and 13.

Examples 1 and 3 were potent at inducing IFN-$\gamma$ and each was more potent than Comparative Example 3 in this assay. Comparative Example 1 was the most potent at inducing IFN-$\gamma$ in this assay. Example 4 and Comparative Example 2 did not induce IFN-$\gamma$ in this assay Example 4 was very potent at inducing IFN-$\alpha$ at a higher dose, being significantly more potent than Examples 1 and 3 in this assay. These three Example compounds were all more potent at inducing IFN-$\alpha$ than Comparative Examples 1, 2 and 3 in this assay. The results for Example 4 were interesting considering that this compound was not active in the HEK hTLR7 reporter assay. It may be that this compound preferentially signals through the IRF-7 pathway.

Examples 1 and 3 and Comparative Example 3 were all potent at inducing TNF-$\alpha$ in this assay. Comparative Example 1 also was potent at inducing TNF-$\alpha$ in this assay. Comparative Example 2 and Example 4 were not significantly effective at inducing TNF-$\alpha$ in this assay.

Figure 14:
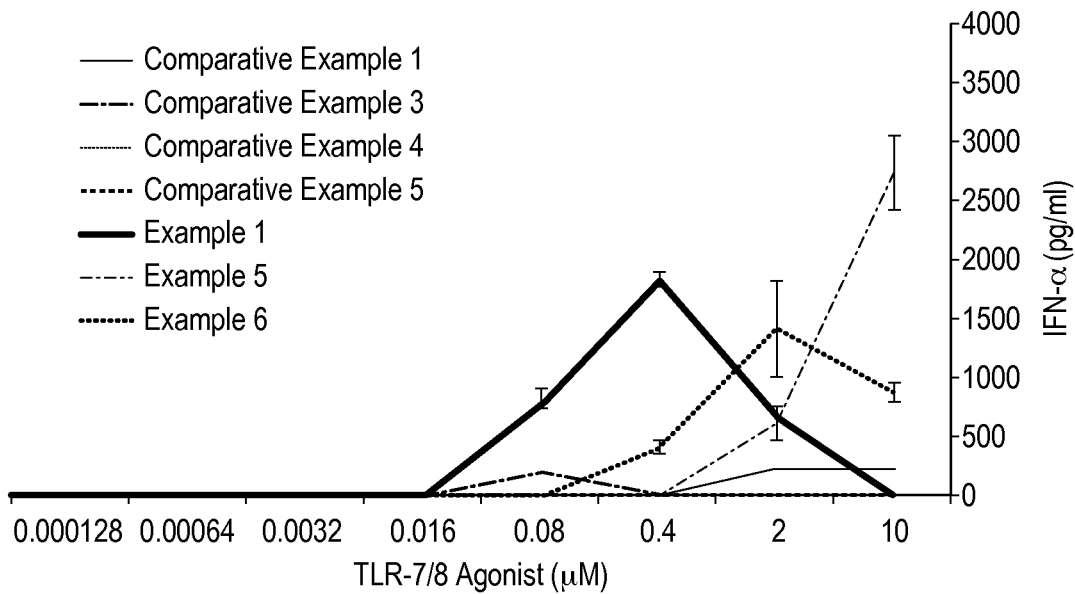
FIG. 14 shows a plot of curves of various compounds tested in the assay for IFN-α induction in hPBMCs
Figure 15:
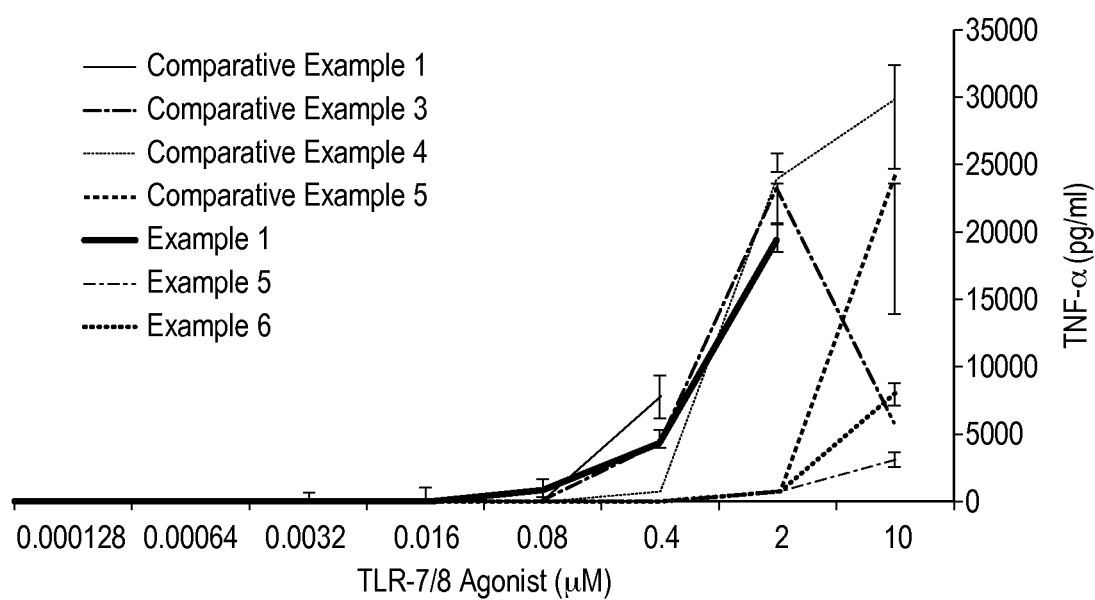
FIG. 15 shows a plot of curves of various compounds tested in the assay for TNF-α induction in hPBMCs

On another occasion, Comparative Examples 1, 3, 4 and 5 and Examples 1, 5, and 6 were tested for their activity in inducing IFN-$\alpha$ and TNF-$\alpha$ in hPBMCs and the results are shown in FIGS. 14 and 15.

Example 1 was very effective at inducing IFN-$\alpha$ in this assay, and Example 6 was also potent, but less so than Example 1. Example 5 was potent but at higher dose. Weaker effects were shown for Comparative Examples 1 and 3. Comparative Example 4 and 5 did not induce IFN-$\alpha$ in this assay.

Example 1 and Comparative Examples 1, 3 and 4, were effective at inducing TNF-$\alpha$ in this assay. Comparative Example 5 and Example 6 were effective but less potent. Example 5 showed a very weak effect in this assay.

Figure 16:
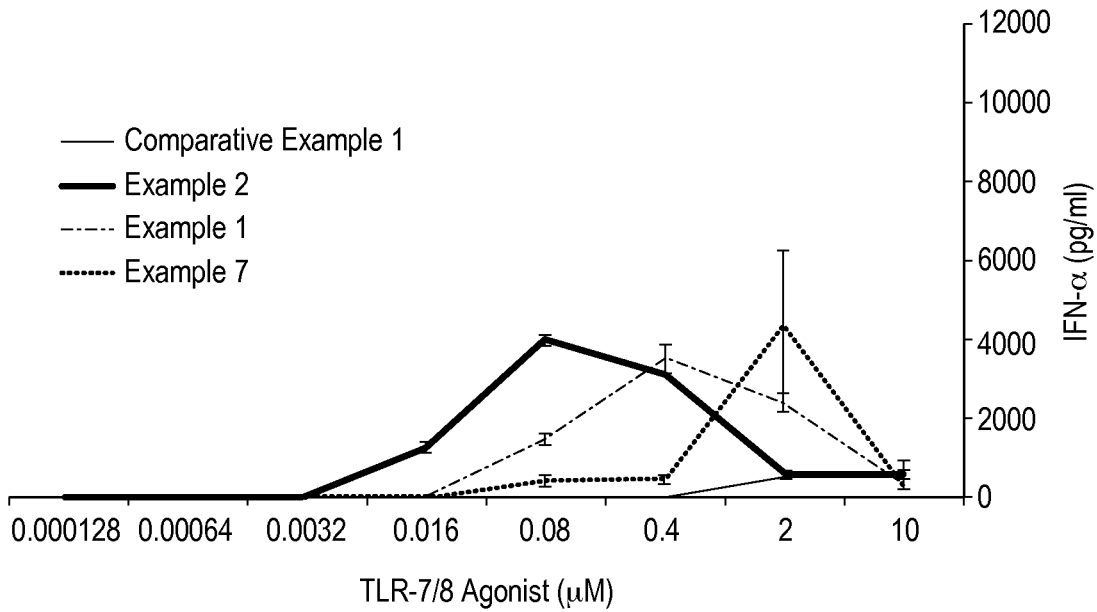
FIG. 16 shows a plot of curves of various compounds tested in the assay for IFN-α induction in hPBMCs
Figure 17:
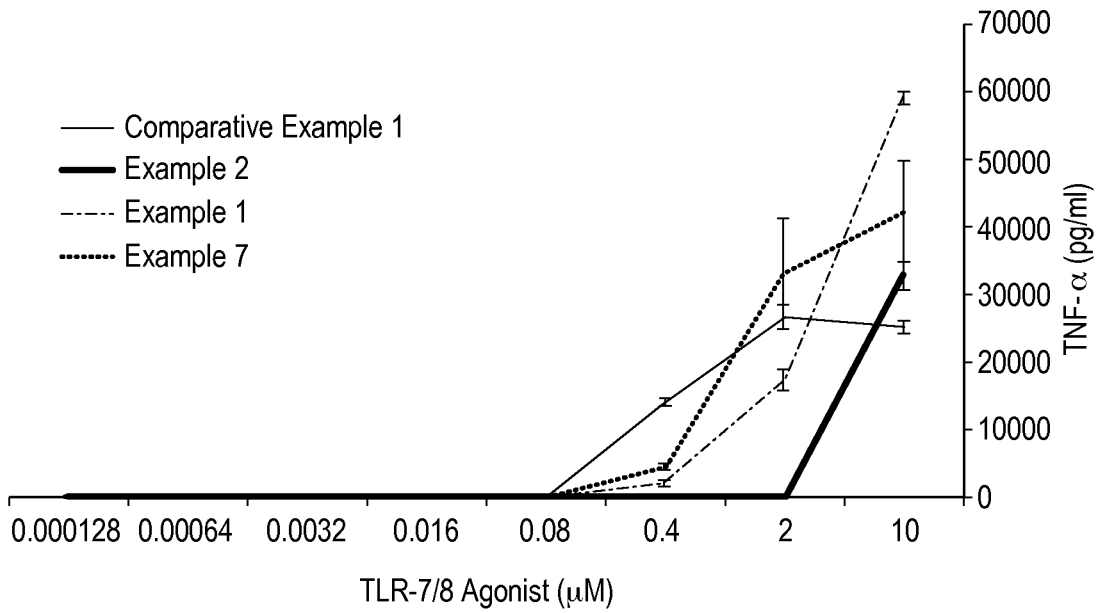
FIG. 17 shows a plot of curves of various compounds tested in the assay for TNF-α induction in hPBMCs

On another occasion, Comparative Example 1 and Examples 1, 2 and 7 were tested for their activity in inducing IFN-$\alpha$ and TNF-$\alpha$ in hPBMCs and the results are shown in FIGS. 16 and 17.

Example 1, 2 and 7 demonstrated good activity in inducing IFN-$\alpha$ with Example 2 being the most potent IFN-$\alpha$ inducer. Comparative Example 1 induced little IFN-$\alpha$.

Examples 1 and 7 and Comparative Example 1 showed similar potency in inducing TNF-$\alpha$. Example 2 was a weaker inducer of TNF-$\alpha$.

The results described herein show that compounds of the invention are effective at agonising hTLR7 and/or hTLR8 and at inducing cytokines and are thus expected to have useful immunostimulatory activity in vivo. They are thus potentially suitable as vaccine adjuvants.

The invention claimed is:
1. A compound of formula (I):

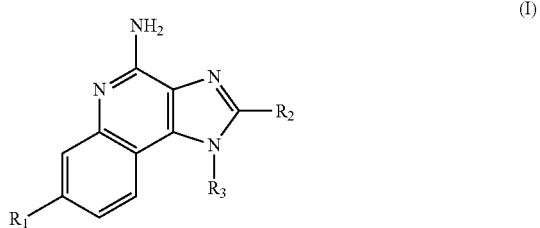

wherein:

$R_1$ represents —O—Z—(P(=O)—OH)—O—Y-A $R_2$ represents H, $C_1$-$C_6$ alkyl, $C_1$-$C_6$ alkylamino, $C_1$-$C_6$ alkoxy, $C_3$-$C_6$ cycloalkyl$C_1$-$C_6$ alkyl, $C_3$-$C_6$ cycloalkyl$C_1$-$C_6$ alkylamino, $C_3$-$C_6$ cycloalkyl$C_1$-$C_6$ alkoxy, $C_1$-$C_6$ alkoxy$C_1$-$C_6$ alkyl, $C_1$-$C_6$ alkoxy$C_1$-$C_6$ alkylamino, $C_1$-$C_6$ alkoxy$C_1$-$C_6$ alkoxy; and optionally terminally substituted with a hydroxyl, amino, —NHNH$_2$, N$_3$, —C≡CH, —COOH, or maleimido group;

Z represents $(C_2$-$C_6$ alkyleneO)$_q$;

Y represents $(C_2$-$C_6$ alkyleneO)$_r$;

q represents an integer 1 to 6;

r represents 0 or an integer 1 to 20;

$R_3$ represents $C_2$-$C_6$ alkylene-OH, $C_2$-$C_6$ alkylene-NH$_2$, $C_2$-$C_5$ alkenyl-CH$_2$—OH or $C_2$-$C_5$ alkenyl-CH$_2$—NH$_2$;

A represents

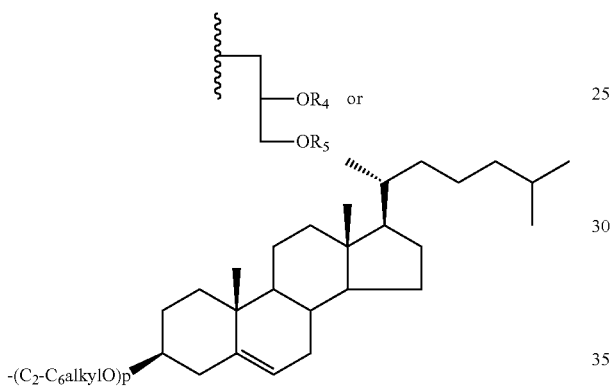

wherein:

$R_4$ represents H, $C_4$-$C_{24}$ alkyl, $C_4$-$C_{24}$ alkenyl, —CO—$C_3$-$C_{23}$ alkyl, or —CO—$C_3$-$C_{23}$ alkenyl;

$R_5$ represents $C_4$-$C_{24}$ alkyl, $C_4$-$C_{24}$ alkenyl, —CO—$C_3$-$C_{23}$ alkyl, or —CO—$C_3$-$C_{23}$ alkenyl;

p represents 0 or an integer 1 to 6;

or a pharmaceutically acceptable salt thereof.

2. The compound according to claim 1 wherein $R_2$ represents H, $C_1$-$C_6$ alkyl or $C_1$-$C_6$ alkoxy$C_1$-$C_6$ alkyl.

3. The compound according to claim 1 wherein r represents 0 or an integer 1 to 3.

4. The compound according to claim 1 wherein $R_3$ represents $C_2$-$C_6$ alkylene-OH.

5. The compound according to claim 1 wherein p represents an integer 1 to 3.

6. The compound according to claim 1 wherein A represents

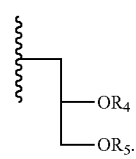

7. The compound according to claim 1 which is a compound of formula (IA):

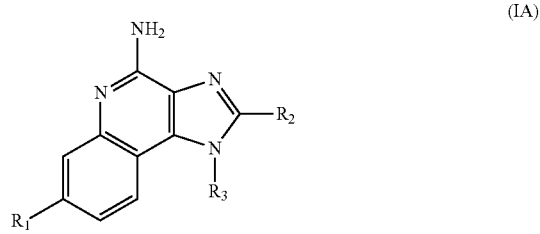

wherein:

$R_1$ represents —O—Z—O—(P(=O)—OH)—O—Y—A $R_2$ represents H, $C_1$-$C_6$ alkyl or $C_1$-$C_3$ alkoxy$C_1$-$C_3$ alkyl;

Z represents $(C_2$-$C_6$ alkyleneO)$_q$;

Y represents $(C_2$-$C_6$ alkyleneO)$_r$;

q represents an integer 1 to 6;

r represents 0 or an integer 1 to 20;

$R_3$ represents $C_2$-$C_6$ alkylene-OH;

A represents

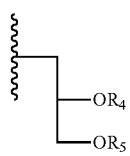

wherein:

$R_4$ represents H, —CO—$C_3$-$C_{23}$ alkyl, or —CO—$C_3$-$C_{23}$ alkenyl;

$R_5$ represents, —CO—$C_3$-$C_{23}$ alkyl, or —CO—$C_3$-$C_{23}$ alkenyl;

or a pharmaceutically acceptable salt thereof.

8. The compound according to claim 7 wherein $R_2$ represents H, n-butyl or CH$_3$CH$_2$OCH$_2$—.

9. The compound according to claim 7 wherein Z represents CH$_2$CH$_2$O.

10. The compound according to claim 7 wherein Y represents ((CH$_2$)$_2$O)$_r$.

11. The compound according to claim 7 wherein q represents an integer 1 to 3.

12. The compound according to claim 7 wherein r represents 0 or an integer 1 to 6.

13. The compound according to claim 12 wherein $R_3$ represents —CH$_2$CH$_2$OH.

14. The compound according to claim 7 wherein $R_4$ represents H and $R_5$ represents —CO—$C_3$-$C_{23}$ alkyl, or —CO—$C_3$-$C_{23}$ alkenyl.

15. The compound according to claim 7 wherein $R_4$ and $R_5$ independently represent —CO—$C_3$-$C_{23}$ alkyl or —CO—$C_3$-$C_{23}$ alkenyl.

16. The compound according to claim 1 selected from:
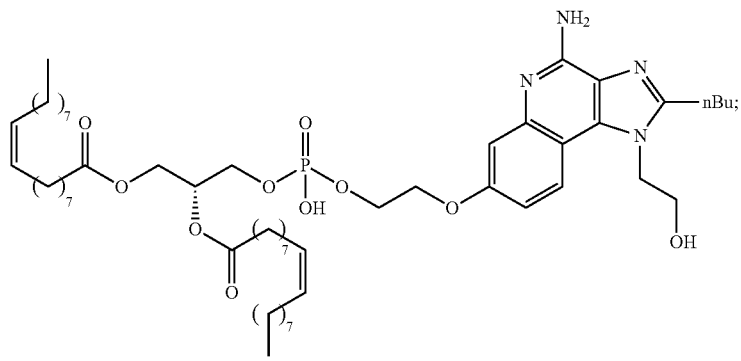
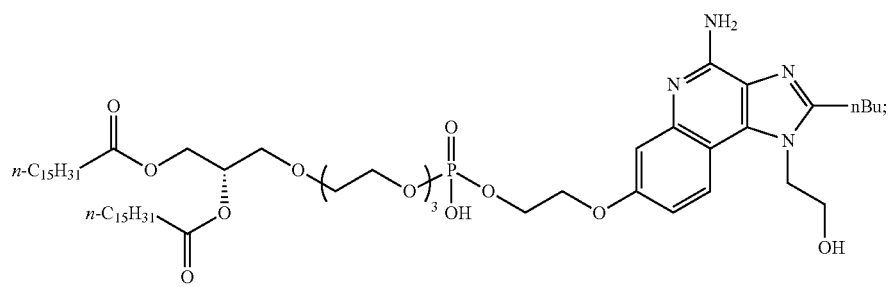
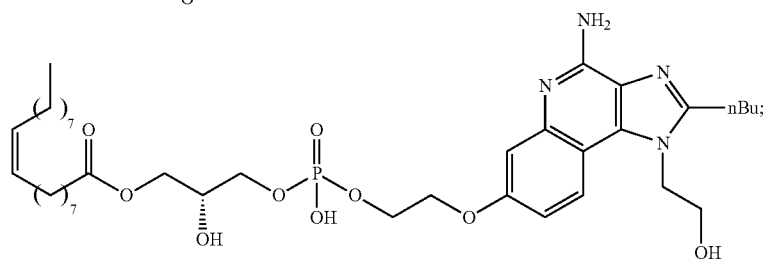
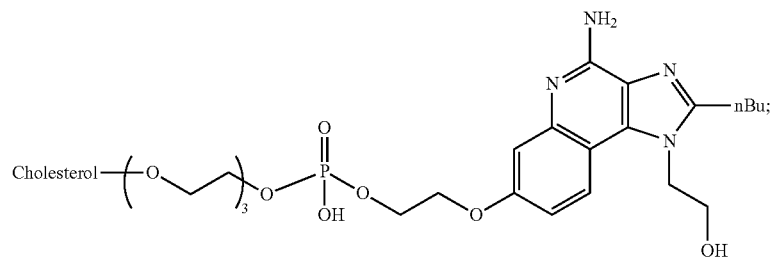
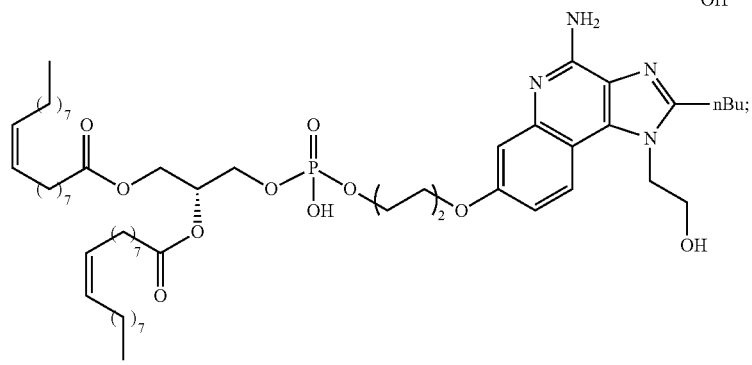

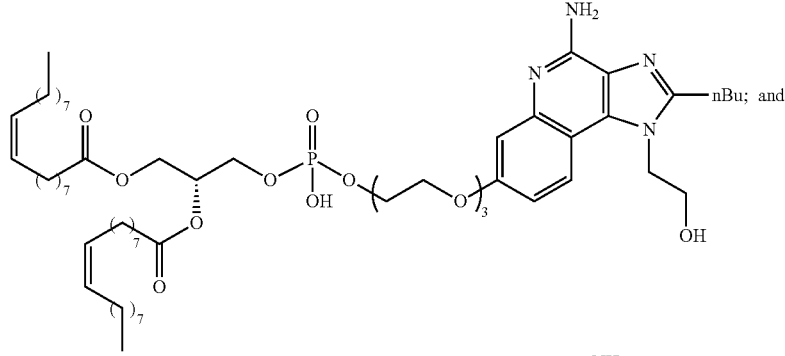

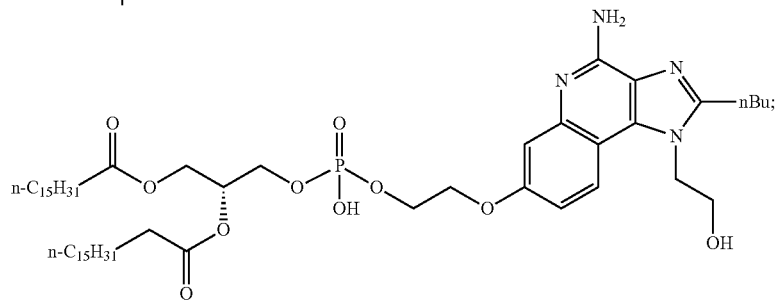

and pharmaceutically acceptable salts thereof.

17. The compound according to claim 14 selected from

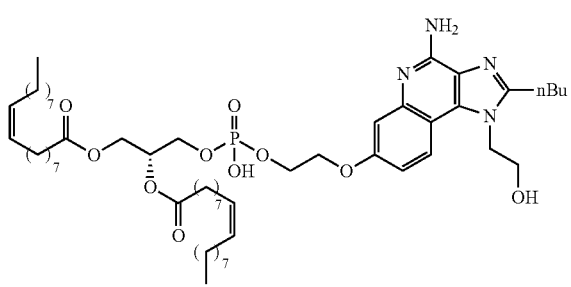

and pharmaceutically acceptable salts thereof.

18. An immunogenic composition comprising a compound according to claim 1 and a vaccine antigen.

19. A method of inducing an immune response in a mammal which comprises administering to said mammal in need thereof an immunostimulatory amount of a compound or composition according to claim 1.

20. A method of inducing protective immunity against a disease in a mammal which comprises administering to a mammal in need thereof an immunostimulatory amount of a compound according to claim 1 together with a disease antigen.

21. A method of treatment of cancer in a mammal which comprises administering to a mammal in need thereof an immunostimulatory amount of a compound according to claim 1 together with a cancer antigen.

22. A method of preparing a choline salt of a compound according to claim 1, comprising:
   (a) dissolving the compound in an aqueous vehicle;
   (b) adding the choline salt; and
   (c) mixing the compound and choline salt;
wherein the method does not include the use of an organic solvent.

23. A method of preparing a choline salt of a compound according to claim 1, comprising:
   (a) dissolving the compound in an organic solvent;
   (b) adding the choline salt;
   (c) mixing the compound and choline salt; and
   (d) removing the organic solvent,
wherein the method does not include a vacuum drying step.

* * * * *